(12) United States Patent
Schimmel et al.

(10) Patent No.: US 7,413,885 B2
(45) Date of Patent: Aug. 19, 2008

(54) TRYPTOPHANYL-TRNA SYNTHETASE-DERIVED POLYPEPTIDES USEFUL FOR THE REGULATION OF ANGIOGENESIS

(75) Inventors: Paul Schimmel, La Jolla, CA (US);
Keisuke Wakasugi, Shizuok (JP);
Martin Friedlander, Del Mar, CA (US)

(73) Assignee: The Scripps Research Institute, La Jolia, CA (US)

( * ) Notice: Subject to any disclaimer, the term of this patent is extended or adjusted under 35 U.S.C. 154(b) by 0 days.

(21) Appl. No.: 11/803,326

(22) Filed: May 14, 2007

(65) Prior Publication Data
US 2007/0218527 A1    Sep. 20, 2007

Related U.S. Application Data

(60) Division of application No. 10/982,014, filed on Nov. 4, 2004, now Pat. No. 7,273,844, which is a continuation-in-part of application No. 10/240,527, filed as application No. PCT/US01/08966 on Mar. 21, 2001, now Pat. No. 7,144,984, which is a continuation-in-part of application No. 10/240,532, filed as application No. PCT/US01/08975 on Mar. 21, 2001, now Pat. No. 7,067,126, said application No. 10/982,014 is a continuation-in-part of application No. 10/080,839, filed on Feb. 22, 2002, now abandoned.

(60) Provisional application No. 60/193,471, filed on Mar. 31, 2000, provisional application No. 60/270,951, filed on Feb. 23, 2001.

(51) Int. Cl.
*C12N 9/10* (2006.01)
*C12N 1/20* (2006.01)
*C12N 15/00* (2006.01)
*C07H 21/04* (2006.01)

(52) U.S. Cl. .................. 435/193; 435/252.3; 435/320.1; 536/23.2

(58) Field of Classification Search .................. 435/193, 435/252.3, 320.2, 320.1; 526/23.2
See application file for complete search history.

(56) References Cited

OTHER PUBLICATIONS

Frolova et al. [Gene, vol. 109, Issue 2, Dec. 30, 1991, pp. 291-296].*

* cited by examiner

*Primary Examiner*—Tekchand Saidha
(74) *Attorney, Agent, or Firm*—Olson & Cepuritis, Ltd.

(57) ABSTRACT

The invention provides an isolated nucleic acid encoding a water-soluble polypeptide fragment of human tryptophanyl-tRNA synthetase, which is useful for the inhibition of angiogenesis. The nucleic acid comprises a polynucleotide of SEQ ID NO: 6, a polynucleotide hybridizable to SEQ ID NO: 6, a polynucleotide that encodes the polypeptide of SEQ ID NO: 7, a polynucleotide that encodes a polypeptide of SEQ ID NO: 12, a polynucleotide that encodes a polypeptide epitope of SEQ ID NO: 7, or a polynucleotide that is hybridizable to a polynucleotide that encodes a polypeptide epitope of SEQ ID NO: 7. Vectors and recombinant cells comprising the nucleic acid are also provided.

20 Claims, 8 Drawing Sheets

Human TrpRS Constructs Summary

|  | Size | pI | Charging | Angiogenic | Angiostatic |
|---|---|---|---|---|---|
| Full-Length TrpRS | 53Kd | 5.7 | + | - | - |
| Mini TrpRS (splice variant) | 48Kd | 5.8 | + | - | + |
| T1 (cleavage product) | 46Kd | 5.9 | + | - | + |
| T2 (cleavage product) | 43Kd | 6.8 | - | - | + |

*Note: A mutant of each of the four proteins has been made in which DLT(205-207) is replaced with ELR

```
1   MPNSEPASLL ELFNSIATQG ELVRSLKAGN ASKDEIDSAV KMLVSLRMSY KAAAGEDYKA DCPPGNPAPT SNHGPDATEA
                                                         ↳ miniTrpRS                    ↳ T1
81  EEDFVDPWTV QTSSAKGIDY DKLIVRFGSS KIDKELINRI ERATGQRPHH FLRRGIFFSH RDMNQVLDAY ENKKPFYLYT
161 GRGPSSEAMH VGH IPFIFT KWLQDVFNVP LVIQMTDDEK YLWKDLTLDQ AYGDAVENAK DIIACGFDIN KTFIFSDLDY
       ↳ T2
241 MGMSSGFYKN VVKIQKHVTF NQVKGIFGFT DSDCIGKISF PAIQAAPSFS NSFPQIFRDR TDIQCLIPCA IDQDPYFRMT
321 RDVAPRIGYP KPALLHSTFF PALQGAQT KM SAS DPNSSIF LTDTAKQIKT KVNKHAFSGG RDTIEEHRQF GGNCDVDVSF
401 MYLTFFLEDD DKLEQIRKDY TSGAMLTGEL KKALIEVLQP LIAEHQARRK EVTDEIVKEF MTPRKLSFDF Q
```

*Note: All are recombinant constructs and have an N-terminal Met and a C-terminal KLAAALEHHHHHH

```
tggcgaatgg gacgcgccct gtagcggcgc attaagcgcg gcgggtgtgg tggttacgcg   60
cagcgtgacc gctacacttg ccagcgccct agcgcccgct cctttcgctt tcttcccttc  120
ctttctcgcc acgttcgccg gctttccccg tcaagctcta aatcggggc tccctttagg  180
gttccgattt agtgctttac ggcacctcga ccccaaaaaa cttgattagg gtgatggttc  240
acgtagtggg ccatcgccct gatagacggt ttttcgccct ttgacgttgg agtccacgtt  300
cttttaatagt ggactcttgt tccaaactgg aacaacactc aaccctatct cggtctattc  360
ttttgattta aagggatttt tgccgatttc ggcctattgg ttaaaaaatg agctgattta  420
acaaaaattt aacgcgaatt ttaacaaaat attaacgttt acaatttcag gtggcacttt  480
tcggggaaat gtgcgcggaa cccctatttg tttatttttc taaatacatt caaatatgta  540
tccgctcatg agacaataac cctgataaat gcttcaataa tattgaaaaa ggaagagtat  600
gagtattcaa catttccgtg tcgcccttat tcccttttttt gcggcatttt gccttcctgt  660
ttttgctcac ccagaaacgc tggtgaaagt aaaagatgct gaagatcagt tgggtgcacg  720
agtgggttac atcgaactgg atctcaacag cggtaagatc cttgagagtt ttcgccccga  780
agaacgtttt ccaatgatga gcacttttaa agttctgcta tgtggcgcgg tattatcccg  840
tattgacgcc gggcaagagc aactcggtcg ccgcatacac tattctcaga atgacttggt  900
tgagtactca ccagtcacag aaaagcatct tacggatggc atgacagtaa gagaattatg  960
cagtgctgcc ataaccatga gtgataacac tgcggccaac ttacttctga caacgatcgg 1020
aggaccgaag gagctaaccg cttttttgca acatggggg atcatgtaa ctcgccttga 1080
tcgttgggaa ccggagctga atgaagccat accaaacgac gagcgtgaca ccacgatgcc 1140
tgcagcaatg gcaacaacgt tgcgcaaact attaactggc gaactactta ctctagcttc 1200
ccggcaacaa ttaatagact ggatggaggc ggataaagtt gcaggaccac ttctgcgctc 1260
ggcccttccg gctggctggt ttattgctga taaatctgga gccggtgagc gtgggtccg 1320
cggtatcatt gcagcactgg ggccagatgg taagccctcc cgtatcgtag ttatctacac 1380
gacggggagt caggcaacta tggatgaacg aaatagacag atcgctgaga taggtgcctc 1440
actgattaag cattggtaac tgtcagacca agtttactca tatatacttt agattgattt 1500
aaaacttcat ttttaattta aaaggatcta ggtgaagatc ctttttgata atctcatgac 1560
caaaatccct taacgtgagt tttcgttcca ctgagcgtca gaccccgtag aaaagatcaa 1620
aggatcttct tgagatcctt ttttttctgcg cgtaatctgc tgcttgcaaa caaaaaaacc 1680
accgctacca gcggtggttt gtttgccgga tcaagagcta ccaactcttt ttccgaaggt 1740
aactggcttc agcagagcgc agataccaaa tactgtcctt ctagtgtagc cgtagttagg 1800
ccaccacttc aagaactctg tagcaccgcc tacatacctc gctctgctaa tcctgttacc 1860
agtggctgct gccagtggcg ataagtcgtg tcttaccggg ttggactcaa gacgatagtt 1920
accggataag gcgcagcggt cgggctgaac ggggggttcg tgcacacagc ccagcttgga 1980
gcgaacgacc tacaccgaac tgagatacct acagcgtgag ctatgagaaa gcgccacgct 2040
tcccgaaggg agaaaggcgg acaggtatcc ggtaagcggc agggtcggaa caggagagcg 2100
cacgagggag cttccagggg gaaacgcctg gtatctttat agtcctgtcg ggtttcgcca 2160
cctctgactt gagcgtcgat ttttgtgatg ctcgtcaggg gggcggagcc tatggaaaaa 2220
cgccagcaac gcggcctttt tacggttcct ggccttttgc tggccttttg ctcacatgtt 2280
ctttcctgcg ttatcccctg attctgtgga taaccgtatt accgcctttg agtgagctga 2340
taccgctcgc cgcagccgaa cgaccgagcg cagcgagtca gtgagcgagg aagcggaaga 2400
gcgcctgatg cggtattttc tccttacgca tctgtgcggt atttcacacc gcatatatgg 2460
tgcactctca gtacaatctg ctctgatgcc gcatagttaa gccagtatac actccgctat 2520
cgctacgtga ctgggtcatg gctgcgcccc gacacccgcc aacacccgct gacgcgccct 2580
gacgggcttg tctgctcccg gcatccgctt acagacaagc tgtgaccgtc tccgggagct 2640
gcatgtgtca gaggttttca ccgtcatcac cgaaacgcgc gaggcagctg cggtaaagct 2700
catcagcgtg gtcgtgaagc gattcacaga tgtctgcctg ttcatccgcg tccagctcgt 2760
tgagtttctc cagaagcgtt aatgtctggc ttctgataaa gcgggccatg ttaagggcgg 2820
ttttttcctg tttggtcact gatgcctccg tgtaagggg atttctgttc atgggggtaa 2880
tgataccgat gaaacgagag aggatgctca cgatacgggt tactgatgat gaacatgccc 2940
ggttactgga acgttgtgag ggtaaacaac tggcggtatg gatgcggcgg gaccagagaa 3000
aaatcactca gggtcaatgc cagcgcttcg ttaatacaga tgtaggtgtt ccacagggta 3060
gccagcagca tcctgcgatg cagatccgga acataatggt gcagggcgct gacttccgcg 3120
tttccagact ttacgaaaca cggaaaccga agaccattca tgttgttgct caggtcgcag 3180
acgttttgca gcagcagtcg cttcacgttc gctcgcgtat cggtgattca ttctgctaac 3240
cagtaaggca accccgccag cctagccggg tcctcaacga caggagcacg atcatgcgca 3300
cccgtggcca ggacccaacg ctgcccgaga tctcgatccc gcgaaattaa tacgactcac 3360
```

FIGURE 6 (cont. - 1)

```
tatagggaga ccacaacggt ttccctctag aaataatttt gtttaacttt aagaaggaga    3420
tatacat atg agt aat cat ggc cca gat gcc aca gaa gct gaa gag gat      3469
        Met Ser Asn His Gly Pro Asp Ala Thr Glu Ala Glu Glu Asp
         1           5                  10 ttt gtg gac cca tgg aca gta cag aca agc agt gca aaa ggc ata gac      3517
Phe Val Asp Pro Trp Thr Val Gln Thr Ser Ser Ala Lys Gly Ile Asp
 15              20                  25                      30 tac gat aag ctc att gtt cgg ttt gga agt agt aaa att gac aaa gag      3565
Tyr Asp Lys Leu Ile Val Arg Phe Gly Ser Ser Lys Ile Asp Lys Glu
             35                  40                  45 cta ata aac cga ata gag aga gcc acc ggc caa aga cca cac cac ttc      3613
Leu Ile Asn Arg Ile Glu Arg Ala Thr Gly Gln Arg Pro His His Phe
         50                  55                  60 ctg cgc aga ggc atc ttc ttc tca cac aga gat atg aat cag gtt ctt      3661
Leu Arg Arg Gly Ile Phe Phe Ser His Arg Asp Met Asn Gln Val Leu
     65                  70                  75 gat gcc tat gaa aat aag aag cca ttt tat ctg tac acg ggc cgg ggc      3709
Asp Ala Tyr Glu Asn Lys Lys Pro Phe Tyr Leu Tyr Thr Gly Arg Gly
         80                  85                  90 ccc tct tct gaa gca atg cat gta ggt cac ctc att cca ttt att ttc      3757
Pro Ser Ser Glu Ala Met His Val Gly His Leu Ile Pro Phe Ile Phe
 95              100                 105                     110 aca aag tgg ctc cag gat gta ttt aac gtg ccc ttg gtc atc cag atg      3805
Thr Lys Trp Leu Gln Asp Val Phe Asn Val Pro Leu Val Ile Gln Met
             115                 120                 125 acg gat gac gag aag tat ctg tgg aag gac ctg acc ctg gac cag gcc      3853
Thr Asp Asp Glu Lys Tyr Leu Trp Lys Asp Leu Thr Leu Asp Gln Ala
         130                 135                 140 tat ggc gat gct gtt gag aat gcc aag gac atc atc gcc tgt ggc ttt      3901
Tyr Gly Asp Ala Val Glu Asn Ala Lys Asp Ile Ile Ala Cys Gly Phe
     145                 150                 155 gac atc aac aag act ttc ata ttc tct gac ctg gac tac atg ggg atg      3949
Asp Ile Asn Lys Thr Phe Ile Phe Ser Asp Leu Asp Tyr Met Gly Met
 160                 165                 170 agc tca ggt ttc tac aaa aat gtg gtg aag att caa aag cat gtt acc      3997
Ser Ser Gly Phe Tyr Lys Asn Val Val Lys Ile Gln Lys His Val Thr
175                 180                 185                 190 ttc aac caa gtg aaa ggc att ttc ggc ttc act gac agc gac tgc att      4045
Phe Asn Gln Val Lys Gly Ile Phe Gly Phe Thr Asp Ser Asp Cys Ile
             195                 200                 205 ggg aag atc agt ttt cct gcc atc cag gct gct ccc tcc ttc agc aac      4093
Gly Lys Ile Ser Phe Pro Ala Ile Gln Ala Ala Pro Ser Phe Ser Asn
         210                 215                 220
```

FIGURE 6 (cont. - 2)

```
tca ttc cca cag atc ttc cga gac agg acg gat atc cag tgc ctt atc    4141
Ser Phe Pro Gln Ile Phe Arg Asp Arg Thr Asp Ile Gln Cys Leu Ile
        225                 230                 235 cca tgt gcc att gac cag gat cct tac ttt aga atg aca agg gac gtc    4189
Pro Cys Ala Ile Asp Gln Asp Pro Tyr Phe Arg Met Thr Arg Asp Val
        240                 245                 250 gcc ccc agg atc ggc tat cct aaa cca gcc ctg ttg cac tcc acc ttc    4237
Ala Pro Arg Ile Gly Tyr Pro Lys Pro Ala Leu Leu His Ser Thr Phe
255                 260                 265                 270 ttc cca gcc ctg cag ggc gcc cag acc aaa atg agt gcc agc gac cca    4285
Phe Pro Ala Leu Gln Gly Ala Gln Thr Lys Met Ser Ala Ser Asp Pro
                275                 280                 285 aac tcc tcc atc ttc ctc acc gac acg gcc aag cag atc aaa acc aag    4333
Asn Ser Ser Ile Phe Leu Thr Asp Thr Ala Lys Gln Ile Lys Thr Lys
                290                 295                 300 gtc aat aag cat gcg ttt tct gga ggg aga gac acc atc gag gag cac    4381
Val Asn Lys His Ala Phe Ser Gly Gly Arg Asp Thr Ile Glu Glu His
        305                 310                 315 agg cag ttt ggg ggc aac tgt gat gtg gac gtg tct ttc atg tac ctg    4429
Arg Gln Phe Gly Gly Asn Cys Asp Val Asp Val Ser Phe Met Tyr Leu
        320                 325                 330 acc ttc ttc ctc gag gac gac gac aag ctc gag cag atc agg aag gat    4477
Thr Phe Phe Leu Glu Asp Asp Asp Lys Leu Glu Gln Ile Arg Lys Asp
335                 340                 345                 350 tac acc agc gga gcc atg ctc acc ggt gag ctc aag aag gca ctc ata    4525
Tyr Thr Ser Gly Ala Met Leu Thr Gly Glu Leu Lys Lys Ala Leu Ile
                355                 360                 365 gag gtt ctg cag ccc ttg atc gca gag cac cag gcc cgg cgc aag gag    4573
Glu Val Leu Gln Pro Leu Ile Ala Glu His Gln Ala Arg Arg Lys Glu
                370                 375                 380 gtc acg gat gag ata gtg aaa gag ttc atg act ccc cgg aag ctg tcc    4621
Val Thr Asp Glu Ile Val Lys Glu Phe Met Thr Pro Arg Lys Leu Ser
        385                 390                 395 ttc gac ttt cag aag ctt gcg gcc gca ctc gag cac cac cac cac cac    4669
Phe Asp Phe Gln Lys Leu Ala Ala Ala Leu Glu His His His His His
        400                 405                 410 cac tgagatccgg ctgctaacaa agcccgaaag gaagctgagt tggctgctgc         4722
His
415 caccgctgag caataactag cataacccct tggggcctct aaacgggtct tgagggtttt  4782
tttgctgaaa ggaggaacta tatccggat                                   4811
```

TRYPTOPHANYL-TRNA SYNTHETASE-DERIVED POLYPEPTIDES USEFUL FOR THE REGULATION OF ANGIOGENESIS

CROSS-REFERENCE TO RELATED APPLICATIONS

This application is a division of U.S. patent application Ser. No. 10/982,014, filed Nov. 4, 2004 now U.S. Pat. No. 7,273,844, which is a continuation-in-part of U.S. patent application Ser. No. 10/240,527, filed Sep. 30, 2002, now U.S. Pat. No. 7,144,984, which is the National Stage of PCT/US01/08966, filed Mar. 21, 2001, which claims the benefit of U.S. Provisional Application for Patent Ser. No. 60/193,471 filed Mar. 31, 2000; and a continuation-in-part of U.S. patent application Ser. No. 10/240,532, filed Sep. 30, 2002, now U.S. Pat. No. 7,067,126, which is the National Stage of PCT/US01/08975, filed Mar. 21, 2001, which also claims the benefit of U.S. Provisional Application for Patent Ser. No. 60/193,471 filed Mar. 31, 2000; and a continuation-in-part of U.S. patent application Ser. No. 10/080,839, filed Feb. 22, 2002, now abandoned, which claims the benefit of U.S. Provisional Application for Patent Ser. No. 60/270,951 filed Feb. 23, 2001; the disclosures of which are incorporated herein by reference.

GOVERNMENTAL RIGHTS

This invention was made with governmental support from the United States Government, National Institutes of Health, Grant GM23562. The United States Government has certain rights in this invention

FIELD OF THE INVENTION

The invention relates to compositions comprising truncated tRNA synthetase polypeptides, as well as nucleic acids encoding such truncated tRNA synthetase polypeptides. Methods of making and using such compositions are also disclosed.

BACKGROUND OF THE INVENTION

Aminoacyl-tRNA synthetases, which catalyze the aminoacylation of tRNA molecules, are ancient proteins that are essential for decoding genetic information during the process of translation. In higher eukaryotes, nine aminoacyl-tRNA synthetases associate with at least three other polypeptides to form a supramolecular multienzyme complex (Mirande et al., *Eur. J. Biochem.* 147:281-89 (1985)). Each of the eukaryotic tRNA synthetases consists of a core enzyme, which is closely related to the prokaryotic counterpart of the tRNA synthetase, and an additional domain that is appended to the amino-terminal or carboxyl-terminal end of the core enzyme (Mirande, *Prog. Nucleic Acid Res. Mol. Biol.* 40:95-142 (1991)).

In most cases, the appended domains appear to contribute to the assembly of the multienzyme complex. However, the presence of an extra domain is not strictly correlated with the association of a synthetase into the multienzyme complex.

Mammalian TrpRS molecules have an amino-terminal appended domain. In normal human cells, two forms of TrpRS can be detected: a major form consisting of the full-length molecule (amino acid residues 1-471 of SEQ ID NO: 1) and a minor truncated form ("mini TrpRS"; amino acid residues 1-424 of SEQ ID NO: 3). The minor form is generated by the deletion of the amino-terminal domain through alternative splicing of the pre-mRNA (Tolstrup et al., *J. Biol. Chem.* 270:397-403 (1995)). The amino-terminus of mini TrpRS has been determined to be the methionine residue at position 48 of the full-length TrpRS molecule (i.e., residue 48 of SEQ ID NO: 1). Alternatively, truncated TrpRS can be generated by proteolysis (Lemaire et al., *Eur. J. Biochem.* 51:237-52 (1975)). For example, bovine TrpRS is highly expressed in the pancreas and is secreted into the pancreatic juice (Kisselev, *Biochimie* 75:1027-39 (1993)), thus resulting in the production of a truncated TrpRS molecule. These results suggest that truncated TrpRS can have a function other than the aminoacylation of tRNA (id.)

Angiogenesis, or the proliferation of new capillaries from pre-existing blood vessels, is a fundamental process necessary for embryonic development, subsequent growth, and tissue repair. Angiogenesis is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g. in the healing of wounds and fractures. Angiogenesis is also a factor in tumor growth, since a tumor must continuously stimulate growth of new capillary blood vessels in order to grow. Angiogenesis is an essential part of the growth of human solid cancer, and abnormal angiogenesis is associated with other diseases such as rheumatoid arthritis, psoriasis, and diabetic retinopathy (Folkman, J. and Klagsbrun, M., *Science* 235:442-447 (1987)).

Several factors are involved in angiogenesis. Both acidic and basic fibroblast growth factor molecules that are mitogens for endothelial cells and other cell types. Angiotropin and angiogenin can induce angiogenesis, although their functions are unclear (Folkman, J., *Cancer Medicine*, pp. 153-170, Lea and Febiger Press (1993)). A highly selective mitogen for vascular endothelial cells is vascular endothelial growth factor or VEGF (Ferrara, N., et al., *Endocr. Rev.* 13:19-32, (1992)).

The vast majority of diseases that cause catastrophic loss of vision do so as a result of ocular neovascularization; age related macular degeneration (ARMD) affects 12-15 million American over the age of 65 and causes visual loss in 10-15% of them as a direct effect of choroidal (sub-retinal) neovascularization. The leading cause of visual loss for Americans under the age of 65 is diabetes; 16 million individuals in the United States are diabetic and 40,000 per year suffer from ocular complications of the disease, often a result of retinal neovascularization. While laser photocoagulation has been effective in preventing severe visual loss in subgroups of high risk diabetic patients, the overall 10-year incidence of retinopathy remains substantially unchanged. For patients with choroidal neovascularization due to ARMD or inflammatory eye disease such as ocular histoplasmosis, photocoagulation, with few exceptions, is ineffective in preventing visual loss. While recently developed, non-destructive photodynamic therapies hold promise for temporarily reducing individual loss in patients with previously untreatable choroidal neovascularization, only 61.4% of patients treated every 3-4 months had improved or stabilized vision compared to 45.9% of the placebo-treated group.

In the normal adult, angiogenesis is tightly regulated, and is limited to wound healing, pregnancy and uterine cycling. Angiogenesis is turned on by specific angiogenic molecules such as basic and acidic fibroblast growth factor (FGF), vascular endothelial growth factor (VEGF), angiogenin, transforming growth factor (TGF), tumor necrosis factor-α (TNF-α) and platelet derived growth factor (PDGF). Angiogenesis can be suppressed by inhibitory molecules such as interferon-α, thrombospondin-1, angiostatin and endostatin. It is the balance of these naturally occurring stimulators and inhibitors that controls the normally quiescent capillary vasculature. When this balance is upset, as in certain disease states, capillary endothelial cells are induced to proliferate, migrate and ultimately differentiate.

Angiogenesis plays a central role in a variety of disease including cancer and ocular neovascularization. Sustained growth and metastasis of a variety of tumors has also been shown to be dependent on the growth of new host blood vessels into the tumor in response to tumor derived angiogenic factors. Proliferation of new blood vessels in response to a variety of stimuli occurs as the dominant finding in the majority of eye disease and that blind including proliferative diabetic retinopathy (PDR), ARMD, rubeotic glaucoma, interstitial keratitis and retinopathy of prematurity. In these diseases, tissue damage can stimulate release of angiogenic factors resulting in capillary proliferation. VEGF plays a dominant role in iris neovascularization and neovascular retinopathies. While reports clearly show a correlation between intraocular VEGF levels and ischemic retinopathic ocular neovascularization, FGF likely plays a role. Basic and acidic FGF are known to be present in the normal adult retina, even though detectable levels are not consistently correlated with neovascularization. This can be largely due to the fact that FGF binds very tightly to charged components of the extracellular matrix and cannot be readily available in a freely diffusible form that would be detected by standard assays of intraocular fluids.

A final common pathway in the angiogenic response involves integrin-mediated information exchange between a proliferating vascular endothelial cell and the extracellular matrix. This class of adhesion receptors, called integrins, are expressed as heterodimers having an α and β subunit on all cells. One such integrin, $\alpha_v\beta_3$, is the most promiscuous member of this family and allows endothelial cells to interact with a wide variety of extracellular matrix components. Peptide and antibody antagonists of this integrin inhibit angiogenesis by selectively inducing apoptosis of the proliferating vascular endothelial cells. Two cytokine-dependent pathways of angiogenesis exist and can be defined by their dependency on distinct vascular cell integrins, $\alpha_v\beta_3$ and $\alpha_v\beta_5$. Specifically, basic FGF- and VEGF-induced angiogenesis depend on integrin $\alpha_v\beta_3$ and $\alpha_v\beta_5$, respectively, since antibody antagonists of each integrin selectively block one of these angiogenic pathways in the rabbit corneal and chick chorioallantoic membrane (CAM) models. Peptide antagonists that block all $\alpha_v$ integrins inhibit FGF- and VEGF-stimulated angiogenesis. While normal human ocular blood vessels do not display either integrin, $\alpha_v\beta_3$ and $\alpha_v\beta_5$ integrins are selectively displayed on blood vessels in tissues from patients with active neovascular eye disease. While only $\alpha_v\beta_3$ was consistently observed in tissue from patients with ARMD, $\alpha_v\beta_3$ and $\alpha_v\beta_5$ both were present in tissues from patients with PDR. Systemically administered peptide antagonists of integrins blocked new blood vessel formation in a mouse model of retinal vasculogenesis.

Hence, anti-angiogenic agents have a role in treating retinal degeneration to prevent the damaging effects of these trophic and growth factors. Angiogenic agents also have a role in promoting desirable vascularization to retard retinal degeneration by enhancing blood flow to cells.

SUMMARY OF THE INVENTION

Tryptophanyl-tRNA synthetase-derived polypeptides, shorter than the ones that occur in nature, have chemokine activity and are useful for research, diagnostic, prognostic and therapeutic applications. In one embodiment, these tRNA synthetase-derived polypeptides are useful for regulating vascular endothelial cell function, and in particular, for inhibiting angiogenesis, especially ocular neovascularization. The polypeptide has the amino acid residue sequence shown in SEQ ID NO: 7, SEQ ID NO: 12, or an angiogenesis inhibiting fragment thereof, the fragment including at least one of amino acid residue signature sequences HVGH (SEQ ID NO: 10) and KMSAS (SEQ ID NO: 11).

These truncated tryptophanyl-tRNA synthetase (TrpRS)-derived polypeptides have an amino-terminal truncation, but can include a Rossmann fold nucleotide binding domain. These polypeptides are capable of regulating vascular endothelial cell function.

A preferred truncated TrpRS-derived polypeptide is a fragment of human TrpRS consisting of the amino acid residue sequence of SEQ ID NO: 12 (i.e., amino acid residues 94-471 of SEQ ID NO: 1). Another preferred TrpRS-derived polypeptide consists of the amino acid residue sequence of SEQ ID NO: 7 (i.e., the $His_6$-tagged version of SEQ ID NO: 12). Preferred angiogenesis-inhibiting fragments of SEQ IS NO: 12 or SEQ ID NO: 7 include fragments bracketed by the signature sequences shown in SEQ ID NO: 10 and SEQ ID NO: 11, or that include at least one of these signature sequences.

In another embodiment, the invention comprises an isolated polynucleotide consisting of a nucleotide sequence at least 95% identical to the sequence of a polynucleotide selected from the group consisting of a polynucleotide of SEQ ID NO: 6, a polynucleotide which is hybridizable to a polynucleotide of SEQ ID NO: 6; a polynucleotide encoding the polypeptide of SEQ ID NO: 7; a polynucleotide encoding the polypeptide of SEQ ID NO: 12, a polynucleotide encoding a polypeptide epitope of SEQ ID NO: 7; and a polynucleotide that is hybridizable to a polynucleotide encoding a polypeptide epitope of SEQ ID NO: 7. The present invention also includes a recombinant expression vector comprising an isolated nucleic acid molecule that encodes any of the aforementioned tryptophanyl-tRNA synthetase-derived polypeptides. Another embodiment is a host cell comprising such a recombinant expression vector.

The invention additionally provides composition and dosage forms that include the truncated tryptophanyl-tRNA synthetase-derived polypeptides together with a pharmaceutically suitable excipient. Such compositions are suitable for intraocular, e.g., intravitreal, sub-retinal or the like, as well as for systemic administration, e.g., transdermal, transmucosal, enteral or parenteral administration.

In another embodiment, the invention provides a method of treating neovascular eye diseases such as age-related macular degeneration, ocular complications of diabetes, rubeotic glaucoma, retinopathy of prematurity, keratitis, ischemic, retinopathy (e.g., sickle cell), pathological myopic, ocular histoplasmosis, pterygia, punitate inner choroidopathy, and the like, by administering an angiogenesis inhibiting amount of the polypeptide together with an appropriate, physiologically compatible excipient or carrier.

BRIEF DESCRIPTION OF THE DRAWINGS

FIG. 1 shows the amino acid residue sequence of tryptophanyl-t-RNA synthetase polypeptide (SEQ ID NO: 1) with included signature sequences (SEQ ID NO: 10 & SEQ ID NO: 11), shown in a box, encompassed also within the truncated form (amino acid residue sequences 94-471 of SEQ ID NO: 1).

FIG. 6 shows the nucleic acid sequence encoding for the TI fragment of human TrpRS, SEQ ID NO: 4.

DETAILED DESCRIPTION OF THE PREFERRED EMBODIMENTS

Definitions

Figure 2:
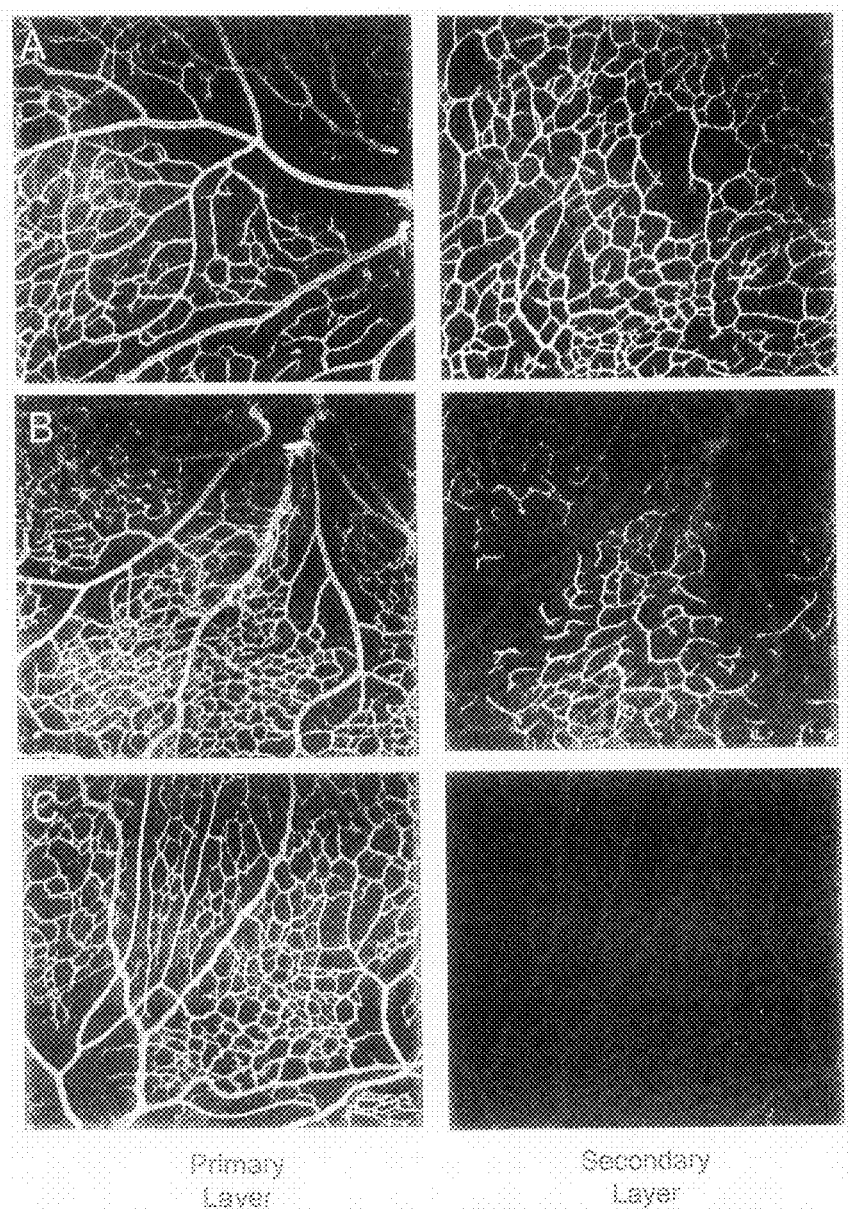
FIG. 2 is a photomicrograph that illustrates the ability of T2 to inhibit vascularization of the secondary deep network of the mouse retina. Row A shows the vascular network of a retina exposed to full length TrpRS. Row B shows the vascular network of a retina exposed to Mini-TrpRS. Row C shows the vascular network of a retina exposed to polypeptide T2 of the present invention. The first (left) column of each Row shows the primary superficial network, and the second column shows the secondary deep network.

"Truncated tRNA synthetase polypeptides" means polypeptides that are shorter than the corresponding full length tRNA synthetase.

"TrpRS" means tryptophanyl-tRNA synthetase.

"Cell culture" encompasses both the culture medium and the cultured cells.

The phrase "isolating a polypeptide from the cell culture" encompasses isolating a soluble or secreted polypeptide from the culture medium as well as isolating an integral membrane protein from the cultured cells.

"Cell extract" includes culture media, especially spent culture media from which the cells have been removed. A cell extract that contains the DNA or protein of interest should be understood to mean a homogenate preparation or cell-free preparation obtained from cells that express the protein or contain the DNA of interest.

"Plasmid" is an autonomous, self-replicating extrachromosomal DNA molecule and is designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but can vary in accordance with the supplier's instructions. After digestion the reaction is subjected to electrophoresis directly on a poly-acrylamide gel to isolate the desired fragment. The nucleotides present in various DNA and RNA fragments are designated herein by the standard single letter designations (A, T, C, G, U) used in the art.

"Polynucleotide" embodying the present invention can be in the form of RNA or in the form of DNA, which DNA includes cDNA, genomic DNA, and synthetic DNA. The DNA can be double-stranded or single-stranded, and if single stranded can be the coding strand or non-coding (anti-sense) strand. The coding sequence which encodes the mature polypeptide can be identical to the coding sequence shown in SEQ ID NO: 6 or can be a different coding sequence which coding sequence, as a result of the redundancy or degeneracy of the genetic code, encodes the same, mature polypeptide sequence shown in SEQ ID NO: 7.

The term "Polynucleotide encoding a polypeptide" encompasses a polynucleotide which includes only coding sequence for the polypeptide as well as a polynucleotide which includes additional coding and/or non-coding sequence.

"Oligonucleotides" refers to either a single stranded polynucleotide or two complementary polynucleotide strands which can be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Amino acid residue" refers to an amino acid which is part of a polypeptide. The amino acid residues described herein are preferably in the L" isomeric form. However, residues in the D" isomeric form can be substituted for any L-amino acid residue, as long as the desired functional property is retained by the polypeptide. $NH_2$ refers to the free amino group present at the amino terminus of a polypeptide. COOH refers to the free carboxyl group present at the carboxyl terminus of a polypeptide. I All amino acid residue sequences represented herein by formulae have a left to right orientation in the conventional direction of amino-terminus to carboxyl-terminus. In addition, the phrase "amino acid residue" is broadly defined to include the 20 amino acids commonly found in natural proteins, as well as modified and unusual amino acids, such as those referred to in 37 C.F.R. § § 1.821-1.822, and incorporated herein by reference. A dash at the beginning or end of an amino acid residue sequence indicates a peptide bond to a further sequence of one or more amino acid residues or to an amino-terminal group such as $NH_2$ or to a carboxyl-terminal group such as COOH.

In a peptide or protein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

Such substitutions are preferably made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and can be determined empirically or in accord with known conservative substitutions.

"Complementing plasmid" describes plasmid vectors that deliver nucleic acids into a packaging cell line for stable integration into a chromosome in the cellular genome.

"Delivery plasmid" is a plasmid vector that carries or delivers nucleic acids encoding a therapeutic gene or gene that encodes a therapeutic product or a precursor thereof or a regulatory gene or other factor that results in a therapeutic effect when delivered in vivo in or into a cell line, such as, but not limited to a packaging cell line, to propagate therapeutic viral vectors.

A variety of vectors is described herein. For example, one vector is used to deliver particular nucleic acid molecules into a packaging cell line for stable integration into a chromosome. These types of vectors are generally identified herein as complementing plasmids. A further type of vector described herein carries or delivers nucleic acid molecules in or into a cell line (e.g., a packaging cell line) for the purpose of propagating therapeutic viral vectors; hence, these vectors are generally referred to herein as delivery plasmids. A third "type" of vector described herein is used to carry nucleic acid molecules encoding therapeutic proteins or polypeptides or regulatory proteins or are regulatory sequences to specific cells or cell types in a subject in need of treatment; these vectors are generally identified herein as therapeutic viral vectors or recombinant adenoviral vectors or viral Ad-derived vectors and are in the form of a virus particle encapsulating a viral nucleic acid containing an expression cassette for expressing the therapeutic gene.

"DNA or nucleic acid homolog" refers to a nucleic acid that includes a preselected conserved nucleotide sequence, such as a sequence encoding a therapeutic polypeptide. The term "substantially homologous" refers to a polypeptide having at least 80%, preferably at least 90%, most preferably at least 95% homology therewith or a less percentage of homology or identity and conserved biological activity or function.

The terms "homology" and "identity" are often used interchangeably. In this regard; degree of homology or identity can be determined, for example, by comparing sequence information using a GAP computer program. The GAP program utilizes the alignment method of Needleman and Wunsch, *J. Mol. Biol.* 48:443 (1970), as revised by Smith and Waterman, *Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program can include: (1) a unary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., *Atlas of Protein Sequence and Structure,* National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson and Lipman, *Proc. Natl. Acad. Sci. USA* 85:2444 (1988). Alternatively the BLAST function of the National Center for Biotechnology Information database can be used to determine identity. In general, sequences are aligned so that the highest order match is obtained. "Identity" per se has an art-recognized meaning and can be calculated using published techniques. (See, e.g.: *Computational Molecular Biology,* Lesk, A. M., ed., Oxford University Press, New York, (1988); Smith, D. W., ed., *Biocomputing: Informatics and Genome Projects,* Academic Press, New York, (1993); Griffin, A. M., and Griffin, H. G., eds., *Computer Analysis of Sequence Data, Part I,* Humana Press, New Jersey, (1994); von Heinje, G., *Sequence Analysis in Molecular Biology,* Academic Press, (1987); and Gribskov, M. and Devereux, J., eds., *Sequence Analysis Primer,* M Stockton Press, New York, (1991)). While there exist a number of methods to measure identity between two polynucleotide or polypeptide sequences, the term "identity" is well known to skilled artisans (Carillo, H. & Lipton, D., *SIAM J. Applied Math.* 48:1073 (1988)). Methods commonly employed to determine identity or similarity between two sequences include, but are not limited to, those disclosed in Martin J. Bishop, ed., *Guide to Huge Computers,* Academic Press, San Diego, (1994), and Carillo, H. & Lipton, D., *SIAM J. Applied Math.* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(I):387 (1984)), BLASTP, BLASTN, FASTA (Atschul, S. F., et al., *J. Molec. Biol.* 215:403 (1990)).

The term "identity" represents a comparison between a test and a reference polypeptide or polynucleotide. For example, a test polypeptide can be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g. 10/100 amino acid difference (approximately 90% identity). Differences are defined as nucleic acid or amino acid substitutions, or deletions.

The terms "gene therapy" and "genetic therapy" refer to the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA can in some manner mediate expression of DNA that encodes the therapeutic product, it can encode a product, such as a peptide or RNA that in some manner mediates, directly or indirectly, expression of a therapeutic product. Genetic therapy can also be used to nucleic acid encoding a gene product replace a defective gene or supplement a gene product produced by the mammal or the cell in which it is introduced. The introduced nucleic acid can encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product can be modified prior to introduction into the cells of the afflicted host in order to enhance or otherwise alter the product or expression thereof.

"Heterologous DNA" is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA can also be referred to as foreign DNA. Any DNA that one of skill in the art would recognize or consider as heterologous or foreign to the cell in which it is expressed is herein encompassed by the term "heterologous DNA". Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA can be secreted or expressed on the surface of the cell in which the heterologous DNA has been introduced. Hence, "heterologous DNA" or "foreign DNA", refers to a DNA molecule not present in the exact orientation and position as the counterpart DNA molecule found in the corresponding wild-type adenovirus. It can also refer to a DNA molecule from another organism or species (i.e., exogenous) or from another adenovirus (Ad) serotype.

"Therapeutically effective DNA product" is a product that is encoded by heterologous DNA so that, upon introduction of the DNA into a host, a product is expressed that effectively ameliorates or eliminates the symptoms, manifestations of an inherited or acquired disease, or that cures said disease. Typically, DNA encoding the desired heterologous DNA is cloned into a plasmid vector and introduced by routine methods, such as calcium-phosphate mediated DNA uptake or microinjection, into producer cells, such as packaging cells. After amplification in producer cells, the vectors that contain the heterologous DNA are introduced into selected target cells.

"Expression or delivery vector" refers to any plasmid or virus into which a foreign or heterologous DNA can be inserted for expression in a suitable host cell, i.e., the protein or polypeptide encoded by the DNA is synthesized in the host cell's system. Vectors capable of directing the expression of DNA segments (genes) encoding one or more proteins are referred to herein as "expression vectors." Also included are vectors that allow cloning of cDNA (complementary DNA) from mRNAs produced using reverse transcriptase.

"Gene" is a nucleic acid molecule whose nucleotide sequence encodes RNA or polypeptide. A gene can be either RNA or DNA. Genes can include regions preceding and following the coding region (leader and trailer) as well as intervening sequences (introns) between individual coding segments (exons).

"Isolated" with reference to a nucleic acid molecule, polypeptide, or other biomolecule, means that the nucleic acid or polypeptide has separated from the genetic environment from which the polypeptide or nucleic acid were obtained. It can also mean altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compounds can be substantially purified by the one-step method described in Smith and Johnson, Gene 67:31-40 (1988). The terms "isolated" and "purified" are sometimes used interchangeably. Such polynucleotide could be part of a vector and/or such polynucleotide or polypeptide could be part of a composition, and still be isolated in that such vector or composition is not part of its natural environment.

By "isolated polynucleotide" is meant that the nucleic acid is free of the coding sequences of those genes that, in the naturally-occurring genome of the organism (if any) immediately flank the gene encoding the nucleic acid of interest. Isolated DNA can be single-stranded or double-stranded, and can be genomic DNA, cDNA, recombinant hybrid DNA, or synthetic DNA. It can be identical to a native DNA sequence, or can differ from such sequence by the deletion, addition, or substitution of one or more nucleotides.

"Isolated" or "purified" as it refers to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures can include for example, but are not limited to, ammonium sulfate fractionation, gel filtration, ion exchange change chromatography, affinity chromatography, density gradient centrifugation and electrophoresis.

A preparation of DNA or protein that is "substantially pure" or "isolated" means a preparation free from naturally occurring materials with which such DNA or protein is normally associated in nature. "Essentially pure" should be understood to mean a "highly" purified preparation that contains at least 95% of the DNA or protein of interest.

"Packaging cell line" is a cell line that provides a missing gene product or its equivalent.

"Adenovirus viral particle" is the minimal structural or functional unit of a virus. A virus can refer to a single particle, a stock of particles or a viral genome. The adenovirus (Ad) particle is relatively complex and can be resolved into various substructures.

"Post-transcription regulatory element (PRE)" is a regulatory element found in viral or cellular messenger RNA that is not spliced, i.e. intronless messages. Examples include, but are not limited to, human hepatitis virus, woodchuck hepatitis virus, the TK gene and mouse histone gene. The PRE can be placed before a polyA sequence and after a heterologous DNA sequence.

"Pseudotyping" describes the production of adenoviral vectors having modified capsid protein or capsid proteins from a different serotype than the serotype of the vector itself. One example, is the production of an adenovirus 5 vector particle containing an Ad37 fiber protein. This can be accomplished by producing the adenoviral vector in packaging cell lines expressing different fiber proteins.

"Promoters of interest herein" can be inducible or constitutive.

Inducible promoters will initiate transcription only in the presence of an additional molecule; constitutive promoters do not require the presence of any additional molecule to regulate gene expression. a regulatable or inducible promoter can also be described as a promoter where the rate or extent of RNA polymerase binding and initiation is modulated by external stimuli. Such stimuli include, but are not limited to various compounds or compositions, light, heat, stress and chemical energy sources. Inducible, suppressible and repressible promoters are considered regulatable promoters. Preferred promoters herein, are promoters that are selectively expressed in ocular cells, particularly photoreceptor cells.

"Receptor" refers to a biologically active molecule that specifically binds to (or with) other molecules. The term "receptor protein" can be used to more specifically indicate the proteinaceous nature of a specific receptor.

"Recombinant" refers to any progeny formed as the result of genetic engineering. This can also be used to describe a virus formed by recombination of plasmids in a packaging cell.

"Transgene" or "therapeutic nucleic acid molecule" includes DNA and RNA molecules encoding an RNA or polypeptide. Such molecules can be "native" or naturally-derived sequences; they can also be "non-native" or "foreign" that are naturally- or recombinantly-derived. The term "transgene," which can be used interchangeably herein with the term "therapeutic nucleic acid molecule," is often used to describe a heterologous or foreign (exogenous) gene that is carried by a viral vector and transduced into a host cell. Therapeutic nucleotide nucleic acid molecules include antisense sequences or nucleotide sequences which can be transcribed into antisense sequences. Therapeutic nucleotide sequences (or transgenes) all include nucleic acids that function to produce a desired effect in the cell or cell nucleus into which said therapeutic sequences are delivered. For example, a therapeutic nucleic acid molecule can include a sequence of nucleotides that encodes a functional protein intended for delivery into a cell which is unable to produce that functional protein.

"Vitreous of the eye" refers to a material that fills the chamber behind the lens of the eye (i.e., vitreous humor or vitreous body).

"Promoter region" refers to the portion of DNA of a gene that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences can be cis acting or can be responsive to trans acting factors. Promoters, depending upon the nature of the regulation, can be constitutive or regulated.

"Operatively linked" means that the sequences or segments have been covalently joined into one piece of DNA, whether in single or double stranded form, whereby control sequences on one segment control expression or replication or other such control of other segments. The two segments are not necessarily contiguous, however.

"Package" refers to a solid matrix or material such as glass, plastic (e.g., polyethylene, polypropylene or polycarbonate), paper, foil and the like capable of holding within fixed limits a polypeptide, polyclonal antibody, or monoclonal antibody of the present invention. Thus, for example, a package can be a glass vial used to contain milligram quantities of a contemplated polypeptide or it can be a microtiter plate well to which microgram quantities of a contemplated polypeptide or antibody have been operatively affixed (i.e., linked) so as to be capable of being immunologically bound by an antibody or antigen, respectively.

"Instructions for use" typically include a tangible expression describing the reagent concentration or at least one assay method parameter, such as the relative amounts of reagent and sample to be admixed, maintenance time periods for reagent/ sample admixtures, temperature, buffer conditions and the like.

"Diagnostic system" in the context of the present invention also includes a label or indicating means capable of signaling the formation of an immunocomplex containing a polypeptide or antibody molecule of the present invention.

"Complex" as used herein refers to the product of a specific binding reaction such as an antibody-antigen or receptor-ligand reaction. Exemplary complexes are immunoreaction products.

"Label" and "Indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

Discussion

The polypeptide shown in FIG. 1 as amino acid residues 94-471 of SEQ ID NO: 1 (e.g., SEQ ID NO: 12), as well as that having the amino acid sequence of SEQ ID NO: 7, or the polypeptide encoded by the cDNA of SEQ ID NO: 6, constitute parts of the present invention. In addition to variants of the above polypeptides, the present invention also includes variants of polynucleotides. Included polynucleotide variants can be a naturally occurring allelic variant of the polynucleotide or a non-naturally occurring variant of the polynucleotide. Thus, the present invention includes polynucleotides encoding the same polypeptide as shown in SEQ ID NO: 7, SEQ ID NO: 12, and the polypeptide encoded by the cDNA of SEQ ID NO: 6 as well as variants of such polynucleotides which variants encode for an angiogenesis inhibiting fragment, derivative or analog of the polypeptides of SEQ ID NO: 7 and SEQ ID NO: 12. Such nucleotide variants include deletion variants, substitution variants and addition or insertion variants.

As indicated above, the polynucleotide can have a coding sequence which is a naturally occurring allelic variant of the coding sequence shown in SEQ ID NO: 6. As known in the art, an allelic variant is an alternate form of a polynucleotide sequence which have a substitution, deletion or addition of one or more nucleotides, which does not substantially alter the function of the encoded polypeptide.

As used herein, the term Ti refers to both the polypeptide of SEQ ID NO: 13 and to the $His_6$-tagged polypeptide of SEQ ID NO: 5. A cDNA encoding the polypeptide of SEQ ID NO 5 is SEQ ID NO: 4 (FIG. 6). The term T2, as uses herein, refers to both the polypeptide of SEQ ID NO: 12 and to the $His_6$-tagged polypeptide of SEQ ID NO: 7. The term TrpRS, as uses herein, refers to both the polypeptide consisting of amino acid residues 1-471 of SEQ ID NO: 1 and to the $His_6$-tagged polypeptide of SEQ ID NO: 1.

The present invention also includes polynucleotides wherein the coding sequence for the mature polypeptide can be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention can encode for a mature protein, or for a protein having a prosequence or for a protein having both a prosequence and presequence (leader sequence).

The polynucleotides of the present invention can also have the coding sequence fused in frame to a marker sequence which allows for purification of the polypeptide of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I., et al., *Cell*, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of SEQ ID NO: 6.

When referring to the polypeptide of SEQ ID NO: 7, SEQ ID NO: 12, or to a polypeptide encoded by the polynucleotide of SEQ ID NO: 6, the terms "fragment," "derivative" and "analog" mean a polypeptide portion which retains substantially the same angiostatic (i.e., angiogenesis inhibiting) function or activity as such polypeptide. Thus, an "analog" includes a proprotein which can be activated by cleavage of the proprotein portion to produce an angiostatically active mature polypeptide.

The polypeptide of the present invention can be a recombinant polypeptide, a natural polypeptide or a synthetic polypeptide, preferably a recombinant polypeptide.

The angiogenesis inhibiting fragment, derivative or analog of the polypeptide of SEQ ID NO: 7, SEQ ID NO: 12, or the polypeptide encoded by the polynucleotide of SEQ ID NO: 6 can be (i) one in which one or more of the amino acid residues are substituted with a conserved or non-conserved amino acid residue (preferably a conserved amino acid residue) and such substituted amino acid residue can or can not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The present invention also includes vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the tRNA synthetase polypeptide genes. The culture conditions, such as temperature, pH and the like, are those previously used with the host cell selected for expression, and will be apparent to the ordinarily skilled artisan.

The polynucleotides of the present invention can be utilized for producing corresponding polypeptides by recombinant techniques. Thus, for example, the polynucleotide sequence can be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. A preferred vector is pET20b. However, any other plasmid or vector can be used as long as it is replicable and viable in the host.

As described above, the appropriate DNA sequence can be inserted into the vector by a variety of procedures. In general, the DNA sequence is inserted into an appropriate restriction endonuclease sites by procedures known in the art. Such procedures and others are deemed to be within the scope of those skilled in the art.

The DNA sequence in the expression vector is operatively linked to an appropriate expression control sequence(s) (promoter) to direct mRNA synthesis. Representative examples of such promoters include LTR or SV40 promoter, the *E. coli* lac or trp promoters, the phage lambda $P_L$ promoter and other promoters known to control expression of genes in prokaryotic or eukaryotic cells or their viruses. The expression vector also contains a ribosome binding site for translation initiation and a transcription terminator. The vector can also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as herein above described, as well as an appropriate promoter or control sequence, can be employed to transform an appropriate host to permit the host to express the protein. Representative examples of appropriate hosts include bacterial cells, such as *E. coli, Salmonella typhimurium, Streptomyces;* fungal cells, such as yeast; insect cells, such as *Drosophila* and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example: Bacterial: pQE70, pQE-9 (Qiagen), pBs, phagescript, PsiX174, pBluescript SK, pBsKS, pNH8a, pNH16a, pNH18a, pNH46a (Stratagene); pTrc99A, pKK223-3, pKK233-3, pDR540, PRIT5 (Pharmacia). Eukaryotic: pWLneo, pSV2cat, pOG44, pXT1, pSG (Stratagene) pSVK3, pBPV, PMSG, pSVL (Pharmacia) and pET20B. In one preferred embodiment, the vector is pET20B. However, any other plasmid or vector can be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology,* 1986)).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., *Molecular Cloning: A Laboratory Manual,* Second Edition, Cold Spring Harbor, N.Y., (1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to about 300 base pairs (bp), that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, *Cell,* 23:175 (198 1), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

DNA sequences derived from the SV40 viral genome, for example, SV40 origin, early promoter, enhancer, splice, and polyadenylation sites can be used to provide the required nontranscribed genetic elements.

Polypeptides are recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1-5 mM) of calcium ion present during purification (Price, et al., *J. Biol. Chem.*, 244:917 (1969)). Protein refolding steps can be used, as necessary, in completing configuration of the mature protein. Finally, high performance liquid chromatography (HPLC) can be employed for final purification steps.

The polypeptides of the present invention can be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention can be glycosylated with mammalian or other eukaryotic carbohydrates or can be non-glycosylated.

The polypeptides of the present invention can be modified to improve stability and increase potency by means known in the art. For example, L-amino acids can be replaced by D-amino acids, the amino terminus can be acetylated, or the carboxyl terminus modified, e.g., ethylamine-capped (Dawson, D. W., et al., *Mol. Pharmacol.*, 55: 332-338 (1999)).

The polypeptide of the present invention can also be employed as gene therapy in accordance with the present invention by expression of such polypeptide in vivo.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector is made target specific. Retroviral vectors can be made target specific by inserting, for example, a polynucleotide encoding a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for polynucleotides encoding zinc finger derived-DNA binding polypeptides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, (1981)). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, (1988)).

The composition of the liposome is usually a combination of phospholipids, particularly high-phase-transition-temperature phospholipids, usually in combination with steroids, especially cholesterol. Other phospholipids or other lipids can also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand can be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), can be exploited for the purpose of targeting antibody-zinc finger-nucleotide binding protein-containing liposomes directly to the malignant tumor. Since the zinc finger-nucleotide binding protein gene product can be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or $F(ab')_2$, as long as they bind efficiently to an the antigenic epitope on the target cells. Liposomes can also be targeted to cells expressing receptors for hormones or other serum factors.

There are available to one skilled in the art multiple viral and non-viral methods suitable for introduction of a nucleic acid molecule into a target cell. Genetic manipulation of primary tumor cells is well known in the art. Genetic modification of a cell can be accomplished using one or more techniques well known in the gene therapy field (Mulligan, R. C. *Human Gene Therapy,* 5(4):543-563 (1993)). Viral transduction methods can comprise the use of a recombinant DNA or an RNA virus comprising a nucleic acid sequence that drives or inhibits expression of a protein having sialyltransferase activity to infect a target cell. A suitable DNA virus for use in the present invention includes but is not limited to an adenovirus (Ad), adeno-associated virus (AAV), herpes virus, vaccinia virus or a polio virus. A suitable RNA virus for use in the present invention includes but is not limited to a retrovirus or Sindbis virus. It is to be understood by those skilled in the art that several such DNA and RNA viruses exist that can be suitable for use in the present invention.

Adenoviral vectors are useful for gene transfer into eukaryotic cells, to study eukaryotic gene expression, for vaccine development, and in animal models. Ad-mediated gene therapy has also been utilized in humans, such as for the transfer of the cystic fibrosis transmembrane conductance regulator (CFTR) gene to the lung. Routes for administrating recombinant Ad to different tissues in vivo include, for example, intratracheal instillation, injection into muscle, peripheral intravenous injection and stereotactic inoculation to brain. The adenoviral vector, then, is widely available to one skilled in the art and is suitable for use in the present invention.

Adeno-associated virus (AAV) has recently been introduced as a gene transfer system with potential applications in gene therapy. Wild-type AAV has been reported to demonstrate high-level infectivity, broad host range and specificity in integrating into the host cell genome. Herpes simplex virus type-1 (HSV-1) is attractive as a vector system, especially for use in the nervous system because of its neurotropic property. Vaccinia virus, of the poxvirus family, has also been developed as an expression vector. Each of the above-described vectors are widely available to one skilled in the art and would be suitable for use in the present invention.

Retroviral vectors are capable of infecting a large percentage of the target cells and integrating into the cell genome. Retroviruses were developed as gene transfer vectors relatively earlier than other viruses, and were first used successfully for gene marking and transducing the cDNA of adenosine deaminase (ADA) into human lymphocytes. Preferred retroviruses include lentiviruses. In preferred embodiments, the retrovirus is selected from the group consisting of HIV, BIV and SIV.

"Non-viral" delivery techniques that have been used or proposed for gene therapy include DNA-ligand complexes, adenovirus-ligand-DNA complexes, direct injection of DNA, $CaPO_4$ precipitation, gene gun techniques, electroporation, liposomes and lipofection. Any of these methods are widely available to one skilled in the art and would be suitable for use in the present invention. Other suitable methods are available to one skilled in the art, and it is to be understood that the present invention can be accomplished using any of the available methods of transfection. Several such methodologies have been utilized by those skilled in the art with varying success. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilamellar or multilammellar liposomes can be constructed such that the interior contains a desired chemical, drug, or, as in the instant invention, an isolated DNA molecule.

The cells can be transfected in vivo, ex vivo, or in vitro. The cells can be transfected as primary cells isolated from a patient or a cell line derived from primary cells, and are not necessarily autologous to the patient to whom the cells are ultimately administered. Following ex vivo or in vitro transfection, the cells can be implanted into a host.

In order to obtain transcription of the nucleic acid of the present invention within a target cell, a transcriptional regulatory region capable of driving gene expression in the target cell is utilized. The transcriptional regulatory region can comprise a promoter, enhancer, silencer or repressor element and is functionally associated with a nucleic acid of the present invention. Preferably, the transcriptional regulatory region drives high level gene expression in the target cell. Transcriptional regulatory regions suitable for use in the present invention include but are not limited to the human cytomegalovirus (CMV) immediate-early enhancer/promoter, the SV40 early enhancer/promoter, the JC polyomavirus promoter, the albumin promoter, PGK and the α-actin promoter coupled to the CMV enhancer.

The vectors of the present invention can be constructed using standard recombinant techniques widely available to one skilled in the art. Such techniques can be found in common molecular biology references such as Sambrook, et al., *Molecular Cloning: A Laboratory Manual,* Cold Spring Harbor Laboratory Press (1989), D. Goeddel, ed., *Gene Expression Technology, Methods in Enzymology* series, Vol. 185, Academic Press, San Diego, Calif. (1991), and Innis, et al.

*PCR Protocols: A Guide to Methods and Applications* Academic Press, San Diego, Calif. (1990).

Administration of a polypeptide or a nucleic acid of the present invention to a target cell in vivo can be accomplished using any of a variety of techniques well known to those skilled in the art.

The vectors and compositions of the present invention can be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal infusion techniques, or intraperitoneally. Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The dosage regimen for treating a disorder or a disease with the vectors of this invention and/or compositions of this invention is based on a variety of factors, including the type of disease, the age, weight, sex, medical condition of the patient, the severity of the condition, the route of administration, and the particular compound employed. Thus, the dosage regimen can vary widely, but can be determined routinely using standard methods.

The pharmaceutically active compounds of this invention can be processed in accordance with conventional methods of pharmacy to produce medicinal compositions or agents for administration to patients, including humans and other mammals. For oral administration, the pharmaceutical composition can be in the form of, for example, a liquid, an ocular insert, a capsule, a tablet, a suspension. The pharmaceutical composition is preferably made in the form of a dosage unit containing a given amount of active agent.

For example, these can contain an amount of vector from about $10^3$-$10^{15}$ viral particles, preferably from about $10^6$-$10^{12}$ viral particles. A suitable daily dose for a human or other mammal can vary widely depending on the condition of the patient and other factors, but, once again, can be determined using routine methods. Administration can be by injection of the active agent as a composition together with suitable pharmacologically acceptable carriers such as saline, dextrose, or water.

A preferred method for inhibiting ocular neovascularization in a patient comprises administering to a patient an ocular neovascularization inhibiting amount of a water-soluble polypeptide of SEQ ID NO: 12, SEQ ID NO: 7, or an ocular neovascularization inhibiting fragment thereof, the fragment including at least one of amino acid residue signature sequences HVGH (SEQ ID NO: 10) and KMSAS (SEQ ID NO: 11). Preferably, the administration is effected daily, weekly, monthly, quarterly or semi-annually. When administration is effected daily, a daily dose of about 20 to about 100 micrograms per kilogram body weight of the polypeptide is preferred. When administration is effected quarterly, a quarterly dose of about 2 to about 9 milligrams per kilogram body weight of the polypeptide is preferred. Preferably, the administration is effected by intraocular delivery, such as intravitreal delivery. The administration can be effected by a sustained delivery device, by gene therapy, by cell-based ocular delivery, and the like.

While the nucleic acids and/or vectors of the invention can be administered as the sole active pharmaceutical agent, they can also be used in combination with one or more vectors of the invention or other agents. When administered as a combination, the therapeutic agents can be formulated as separate compositions that are given at the same time or different times, or the therapeutic agents can be given as a single composition.

The polypeptide of the present invention can also be utilized in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention can be employed on conjunction with other therapeutic compounds.

The pharmaceutical compositions can be administered in a convenient manner, such as the intraocular, eye drop, and systemic routes. The amounts and dosage regimens of the tRNA synthetase-derived polypeptides administered to a patient will depend on a number of factors, such as the mode of administration, the nature of the condition being treated, the body weight of the subject being treated and the judgment of the prescribing physician. Generally speaking, the polypeptide is administered in therapeutically effective doses of at least about 10 µg/kg body weight. Preferably, the dosage is about 10 µg/kg body weight to about 1 mg/kg body weight daily, taking into the account the frequency, routes of administration, symptoms, etc.

Angiostatic TrpRS therapy can be used to oppose the angiogenic activity of endogenous and exogenous angiogenic factors, and to prevent the further growth or even regress solid tumors, since angiogenesis and neovascularization are essential steps in solid tumor growth. Such therapies can also be used to treat rheumatoid arthritis, psoriasis and diabetic retinopathy which are all characterized by abnormal angiogenesis.

Compositions are provided containing therapeutically effective amounts and concentrations of recombinant adenovirus delivery vectors for delivery of therapeutic gene products to cells that express a particular receptor. These cells include cells of the eye. Of particular interest are photoreceptor cells of the eye. Administration can be effected by any means through which contacting with the photoreceptors is effected. To provide access to photoreceptor cells, preferable modes of administration include, but are not limited to, subretinal injection or intravitreal injection.

The recombinant viral compositions can also be formulated for implantation into the anterior or posterior chamber of the eye, preferably the vitreous cavity, in sustained released formulations, such as adsorbed to biodegradable supports, including collagen sponges, or in liposomes. Sustained release formulations can be formulated for multiple dosage administration, so that during a selected period of time, such as a month or up to about a year, several dosages are administered. Thus, for example, liposomes can be prepared such that a total of about two to up to about five or more times the single dosage is administered in one injection.

The vectors are formulated in an ophthalmologically acceptable carrier for intraocular, preferably intravitreal, administration in a volume of between about 0.05 ml and 0.15 ml, preferably about 0.05 and 0.1 ml.

The compositions can be provided in a sealed sterile vial containing an amount of the active agent that upon intraocular administration delivers a sufficient amount of viral particles to the photoreceptors in a volume of about 50 to 150 µl, containing at least about $10^7$, more preferably at least about $10^8$ plaque forming units in such volume. Typically, the vials will, thus, contain about 0.15 ml of the composition.

To prepare such compositions, the viral particles are dialyzed into a suitable ophthalmologically acceptable carrier or viral particles can be concentration and/or mixed therewith. The resulting mixture can be a solution, suspension or emulsion. In addition, the viral particles can be formulated as the sole pharmaceutically active ingredient in the composition or can be combined with other active agents for the particular disorder treated.

For administration by intraocular injection or via eye drops, suitable carriers include, but are not limited to, physiological saline, phosphate buffered saline (PBS), balanced salt solution (BSS), Ringers lactate solution, and solutions containing thickening and solubilizing agents, such as glucose, polyethylene glycol, and polypropylene glycol and mixtures thereof. Liposomal suspensions can also be suitable as pharmaceutically acceptable carriers. These can be prepared according to methods known to those skilled in the art. Suitable ophthalmologically acceptable carriers are known. Solutions or mixtures intended for ophthalmic use can be formulated as 0.01% -10% (w/w) isotonic solutions, pH about 5-7, with appropriate salts (see, e.g., U.S. Pat. No. 5,116,868, which describes typical compositions of ophthalmic irrigation solutions and solutions for local application). Such solutions, which have a pH adjusted to about 7.4, contain, for example, 90-100 mM sodium chloride, 4-6 mM dibasic potassium phosphate, 4-6 mM dibasic sodium phosphate, 8-12 mM sodium citrate, 0.5-1.5 mM magnesium chloride, 1.5-2.5 mM calcium chloride, 15-25 mM sodium acetate, 10-20 mM sodium D,L-β-hydroxybutyrate and 5-5.5 mM glucose.

The compositions can be prepared with carriers that protect the active agent against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and other types of implants that can be placed directly into the anterior or posterior chamber or vitreous cavity of the eye. The compositions can also be administered in pellets, such as ELVAX® pellets (ethylene-vinyl acetate copolymer resin, DuPont).

Liposomal suspensions, including tissue-targeted liposomes, can also be suitable as pharmaceutically acceptable carriers. For example, liposome formulations can be prepared by methods known to those of skill in the art (see, e.g., Kimm et al. *Bioch. Bioph. Acta* 728:339-398 (1983); Assil et al. Arch Ophthalmol. 105:400 (1987); and U.S. Pat. No. 4,522,811). The viral particles can be encapsulated into the aqueous phase of liposome systems.

The active materials or agents can also be mixed with other active materials, that do not impair the desired action, or with materials that supplement the desired action or have other action, including viscoelastic materials, such as hyaluronic acid, which is sold under the trademark HEALON® (Pharmacia, Inc), which is a solution of a high molecular weight (MW) of about 3 millions fraction of sodium hyaluronate (see, e.g., U.S. Pat. Nos. 5,292,362, 5,282,851, 5,273,056, 5,229,127, 4,517,295 and 4,328,803), and a resins sold under the trademark VISCOAT® ( available from Alcon Surgical, Inc.), which are fluorine-containing (meth)acrylates, such as, 1H,1H,2H,2H-heptadecafluorodecylmethacrylate (see, e.g., U.S. Pat. Nos. 5,278,126, 5,273,751 and 5,214,080; and resins sold under the trademark ORCOLON® (Optical Radiation Corporation, see e.g., U.S. Pat. No. 5,273,056), and methylcelluloses, methyl hyaluronates, polyacrylamides and polymethacrylamides (see e.g., U.S. Pat. No. 5,273,751). The viscoelastic materials are present generally in amounts ranging from about 0.5 to 5%, preferably 1 to 3% by weight of the conjugate material and serve to coat and protect the treated tissues. The compositions can also include a dye, such as methylene blue or other inert dye, so that the composition can be seen when injected into the eye. Additional active agents can be included.

The compositions can be enclosed in ampules, disposable syringes or multiple or single dose vials made of glass, plastic or other suitable material. Such enclosed compositions can be provided in kits. In particular, kits containing vials, ampules or other container, preferably disposable vials with sufficient amount of the composition to deliver about 0.1 ml thereof, and disposable needles, preferably self sealing 25-33 gauge needles, or smaller, are provided herein.

Finally, the compositions can be packaged as articles of manufacture containing packaging material, typically a vial, an ophthalmologically acceptable composition containing a polypeptide of the present invention and a label that indicates the therapeutic use of the composition.

Also provided are kits for practice of the methods herein. The kits contain one or more containers, such as sealed vials, with sufficient composition for single dosage administration, and one or more needles, such as self sealing 25-33 gauge or smaller needles, preferably 33 gauge or smaller needles, with precisely calibrated syringes or other precisely calibrated delivery device, suitable for intravitreal injection.

Administration of the composition is preferably by intraocular injection, although other modes of administration can be effective, if the sufficient amount of the compound achieves contact with the vitreous cavity. Intraocular injection can be effected by intravitreal injection, aqueous humor injection or injection into the external layers of the eye, such as subconjunctival injection or subtenon injection, or by topical application to the cornea, if a penetrating formulation is used.

For any particular patient, specific dosage regimens should be adjusted over time according to the individual need and the professional judgment of the person administering or supervising the administration of the recombinant viruses. The concentration and amount ranges set forth herein are exemplary only and are not intended to limit the scope or practice of the claimed methods.

The present invention also provides a method of assaying the angiogenesis inhibiting activity of a composition. The method comprises injecting a solution of a composition to be assayed into an eye of a newborn mouse on about day 7 or 8 postnatal (i.e., about 7 to 8 days after the mouse is born). The mouse is euthanized on about day 12 or 13 postnatal and the injected eye is removed. The retina is excised from the injected eye and stained with a rabbit anti-mouse collagen IV antibody and a fluorescent-labeled goat anti-rabbit IgG antibody to visualize the vascular network of the retina. The degree of vascularization of the deep outer vascular plexus of the stained retina exposed to the composition to be assayed is microscopically compared with the degree of vascularization of a retina from the eye of a control mouse of the same age that has been similarly stained and which was not exposed to the composition. A substantially lower level of vascularization in the retina of the mouse exposed to the composition to be assayed relative to the control mouse indicates inhibition of angiogenesis by that composition.

The Examples that follow are illustrative of specific embodiments of the invention, and of various uses thereof. They are provided for illustrative and explanatory purposes only, but are not to be taken as limiting.

EXAMPLE 1

Preparation of Endotoxin-Free Recombinant TrpRS

Endotoxin-free recombinant human TrpRS was prepared as follows. Plasmids encoding full-length TrpRS (amino acid residues 1-471 of SEQ ID NO: 1), or truncated TrpRS, hereinafter referred to as T2 (SEQ ID NO: 12), consisting essentially of residues 94-471 of SEQ ID NO: 1 (i.e., residues 94-471 of full-length TrpRS) and a second truncated TrpRS, hereinafter referred to as TI (SEQ ID NO: 13), consisting essentially of residues 71-471 of SEQ ID NO: 1 were prepared. Each plasmid also encoded a C-terminal tag comprising six histidine residues (e.g. amino acid residues 472-484 of SEQ ID NO: 1), and an initial methionine residue. The $His_6$-tagged T1 has the amino acid sequence of SEQ ID NO: 5, whereas the $His_6$-tagged T2 has the amino acid sequence of SEQ ID NO: 7.

The above plasmids were introduced into E. coli strain BL 21 (DE 3) (Novagen, Madison, Wis.). Human mature EMAPII, also encoding a C-terminal tag of six histidine residues, was similarly prepared for use. Overexpression of recombinant TrpRS was induced by treating the cells with isopropyl β-D-thiogalactopyranoside for 4 hours. Cells were then lysed and the proteins from the supernatant purified on HIS-BIND® nickel affinity columns (Novagen) according to the manufacturer's suggested protocol. Following purification, TrpRS proteins were incubated with phosphate-buffered saline (PBS) containing 1 μM $ZnSO_4$ and then free $Zn^{2+}$ was removed (Kisselev et al., *Eur. J. Biochem.* 120:511-17 (1981)).

Endotoxin was removed from protein samples by phase separation using Triton X-114 (Liu et al., *Clin. Biochem.* 30:455-63 (1997)). Protein samples were determined to contain less than 0.01 units of endotoxin per mL using an E-TOX-ATE® gel-clot assay (Sigma, St. Louis, Mo.). Protein concentration was determined by the Bradford assay (Bio-Rad, Hercules, Calif.) using bovine serum albumin (BSA) as a standard.

EXAMPLE 2

Cleavage of Human TrpRS by PMN Elastase

Cleavage of human full-length TrpRS by PMN elastase was examined. TrpRS was treated with PMN elastase in PBS (pH 7.4) at a protease:protein ratio of 1:3000 for 0, 15, 30, or 60 minutes. Following cleavage, samples were analyzed on 12.5% SDS-polyacrylamide gels. PMN elastase cleavage of a full-length TrpRS of about 53 kDa, encoded by nucleotides 3428 to 4738 of DNA SEQ ID NO: 2) generated a major fragment of about 46 kDa (SEQ ID NO: 5, T1 having the C-terminal histidine tag) and a minor fragment of about 43 kDa (SEQ ID NO: 7, T2 having the C-terminal histidine tag).

Western blot analysis with antibodies directed against the carboxyl-terminal $His_6$-tag of the recombinant TrpRS protein revealed that both fragments possessed the $His_6$-tag at their carboxyl-terminus. Thus, only the amino-terminus of two TrpRS fragments has been truncated. The amino-terminal sequences of the TrpRS fragments were determined by Edman degradation using an ABI Model 494 sequencer. Sequencing of these fragments showed that the amino-terminal sequences were S-N-H-G-P (SEQ ID NO: 8) and S-A-K-G-I (SEQ ID NO: 9), indicating that the amino-terminal residues of the major and minor TrpRS fragments were located at positions 71 and 94, respectively, of full-length TrpRS. These human TrpRS constructs are summarized in FIG. 1. Signature sequences -HVGH- (SEQ ID NO: 10) and -KMSAS- (SEQ ID NO: 11) are shown in boxes.

The angiostatic activity of the major and minor TrpRS fragments was analyzed in angiogenesis assays. Recombinant forms of the major and minor TrpRS fragments SEQ ID NO: 5 and SEQ ID NO: 7 each having a C-terminal histidine tag (amino acid residues 472-484 of SEQ ID NO: 1) were used in these assays. Both TrpRS fragments were capable of inhibiting angiogenesis.

EXAMPLE 3

Truncated Fragments of Trp-RS Show Potent

Angiostatic Effect for Retinal Angiogenesis. Angiostatic activity of truncated forms derived from tryptophanyl-rRNA synthetase (TrpRs, 53 kDa; SEQ ID NO: 1) was examined, in a post-natal mouse retinal angiogenesis model Friedlander et al. Abstracts 709-B84 and 714-B89, *IOVS* 41(4):138-139 (Mar. 15, 2000) has reported that postnatal retinal angiogenesis proceeds in stages in the mouse. The present invention provides a method of assaying angiogenesis inhibition by exploiting this staged retinal vascularization.

Endotoxin-free recombinant mini-TrpRS (48 kDa splice variant of histidine tagged TrpRS; SEQ ID NO: 3) and T2 (43 kDa cleavage product of histidine tagged TrpRS; SEQ ID NO: 7) were prepared as recombinant proteins. These proteins were injected intra-vitreally into neonatal Balb/C mice on postnatal (P) day 7 or 8 and the retinas harvested on P12 or P13. Collagen IV antibody and fluorescein-conjugated secondary antibody were used to visualize the vessels in retinal whole mount preparations. Anti-angiogenic activity was evaluated by confocal microscopic examination based upon the effect of injected proteins on formation of the deep, outer, vascular plexus. Intra-vitreous injection and retina isolation was performed with a dissecting microscope (SMZ 645, Nikon, Japan). An eyelid fissure was created in postnatal day 7 (P7) mice with a fine blade to expose the globe for injection of T2 (5 pmol) or TrpRS (5 pmol). The samples (0.5 μl) were injected with a syringe fitted with a 32-gauge needle (Hamilton Company, Reno, Nev.). The injection was made between the equator and the corneal limbus; during injection the location of the needle tip was monitored by direct visualization to determine that it was in the vitreal cavity. Eyes with needle-induced lens or retinal damage were excluded from the study. After the injection, the eyelids were repositioned to close the fissure.

On postnatal day 12 (P12), animals were euthanized and eyes enucleated. After 10 minutes in 4% paraformaldehyde (PFA) the cornea, lens, sclera, and vitreous were excised through a limbal incision. The isolated retina was prepared for staining by soaking in methanol for 10 minutes on ice, followed by blocking in 50% fetal bovine serum (Gibco, Grand Island, N.Y.) with 20% normal goat serum (The Jackson Laboratory, Bar Harbor, Me.) in PBS for 1 hour on ice. The blood vessels were specifically visualized by staining the retina with a rabbit anti-mouse collagen IV antibody (Chemicon, Temecula, Calif.) diluted 1:200 in blocking buffer for 18 h at 4° C. An ALEXA FLUOR® 594-conjugated goat anti-rabbit IgG antibody (Molecular Probes, Eugene, Oreg.)

(1:200 dilution in blocking buffer) was incubated with the retina for 2 h at 4° C. The retinas were mounted with slow-fade mounting media M (Molecular Probes, Eugene, Oreg.).

Angiostatic activity was evaluated based upon the degree of angiogenesis in the deep, outer retinal vascular layer (secondary layer) that forms between P8 and P12. The appearance of the inner blood vessel network (primary layer) was evaluated for normal development and signs of toxicity. None of the protein constructs used in this example produced any adverse effects on the primary layer.

FIG. 2 provides a photomicrographic depiction of the ability of T2 to inhibit vascularization of the secondary deep network of the mouse retina. In FIG. 2, row A shows the vascular network of a retina exposed to TrpRS, Row B shows the vascular network of a retina exposed to Mini-TrpRS, and row C shows the vascular network of a retina exposed to polypeptide T2 of the present invention. The first (left) column shows the primary superficial network, and the second column shows the secondary deep network. As is evident from FIG. 2, none of the polypeptides affected the primary superficial network, whereas only T2 significantly inhibited vascularization of the secondary deep network.

Figure 3:
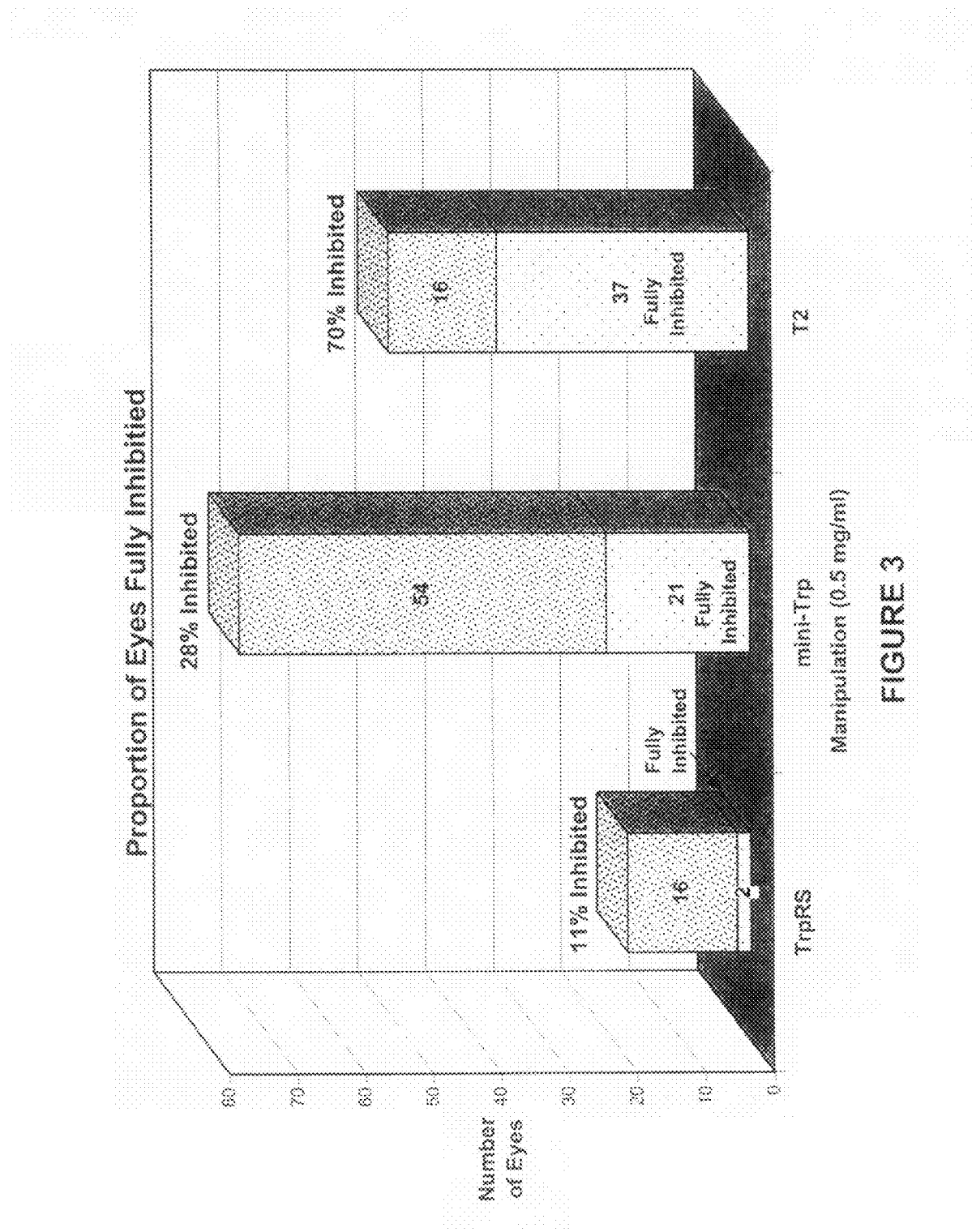
FIG. 3 is a graphical representation of data reported in Example 3, below.

Most PBS-treated eyes exhibited normal retinal vascular development, but complete inhibition of the outer vascular layer was observed in about 8.2% (n=73) of the treated eyes. Complete inhibition of the outer network was observed in 28% of mini-TrpRS (0.5 mg/ml)-treated eyes (n=75). The smaller, truncated form (T2) was a far more potent inhibitor of angiogenesis in a dose dependent fashion; 14.3% were completely inhibited after treatment with 0.1 mg/ml of T2 (n=14), 40% after treatment with 0.25 mg/ml (n=20) and 69.8% inhibited completely after 0.5 mg/ml (n=53). The data for the 0.5 mg/ml treatments are presented graphically in FIG. 3. Extracts of mouse retina contain a protein with the same apparent molecular mass and immunoreactivity as human mini-TrpRS, as analyzed by SDS-PAGE and Western Blot. Full-length mouse and human TrpRS share about 88% amino acid identity and contain 475 and 471 amino acids, respectively. Truncated forms of TrpRS, especially T2, have a potent angiostatic effect on retinal vascular development.

EXAMPLE 4

Matrigel Angiogenesis Assay

A mouse matrigel angiogenesis assay was used to examine the angiostatic activity of T2 (SEQ ID NO: 7) according to the methods described by Brooks et al. *Methods Mol. Biol.*, 129: 257-269 (1999) and Eliceiri et al. *Mol. Cell*, 4: 915-924 (1999). It was performed as described with the following modifications. Athymic wehi mice were subcutaneously implanted with 400 μl growth-factor depleted matrigel (Becton Dickinson, Franklin Lakes, N.J.) containing 20 nM VEGF. The angiostatic activity of T2 was initially tested by including 2.5 μM T2 in the matrigel plug. The potency was determined by including various concentrations of T2 in the plug. On day 5, the mice were intravenously injected with the fluorescein-labeled endothelial binding lectin Griffonia (Bandeiraea) Simplicifolia I, isolectin B4 (Vector Laboratories, Burlingame, Calif.) and the matrigel plugs were resected. The fluorescein content of each plug was quantified by spectrophotometric analysis after grinding the plug in RIPA buffer (10 mM sodium phosphate, pH 7.4, 150 mM sodium chloride, 1% Nonidet P-40, 0.5% sodium deoxycholate, 0.1% sodium dodecyl sulfate).

EXAMPLE 5

Localization of T2 Binding within the Retina

To assess the uptake and localization of T2 injected into the retina, fluorescein-labeled (ALEXA® 488, Molecular Probes, Inc., Eugene Oreg.) T2 was injected into the vitreous of the eye on postnatal day 7 (P7). Globes were harvested on P8 and P12 and fixed in 4% PFA for 15 min. The retinas were further dissected free of adherent nonretinal tissue and placed in 4% PFA overnight at 4° C. and then embedded in medium (TISSUE-TEK® O.C.T., Sakura FineTechnical Co., Japan) on dry ice. Cryostat sections (10 micron) were rehydrated with PBS and blocked with 5% BSA, 2% normal goat serum in PBS. Blood vessels were visualized with anti-mouse collagen IV antibody as described above. VECTASHIELD® containing DAPI nuclear stain (Vector Laboratories, Burlingame, Calif.) was used to mount the tissues with a cover slip.

Alternatively, unstained retina sections were incubated with 200 nM fluorescein-labeled full-length TrpRS or fluorescein-labeled T2 in blocking buffer overnight at 4° C. Sections were washed six times for 5 minutes each in PBS, followed by incubation with 1 μg/ml DAPI for 5 minutes for visualization of the nuclei. Pre-blocking with unlabeled T2 was performed by incubating 1 μM unlabeled T2 for 8 hours at 4° C. prior to incubation with fluorescein-labeled T2. Retinas were examined with a multiphoton BioRad MRC1024 confocal microscope. 3-D vascular images were produced from a set of Z-series images using the Confocal Assistant software (BioRad, Hercules, Calif.).

Figure 4:
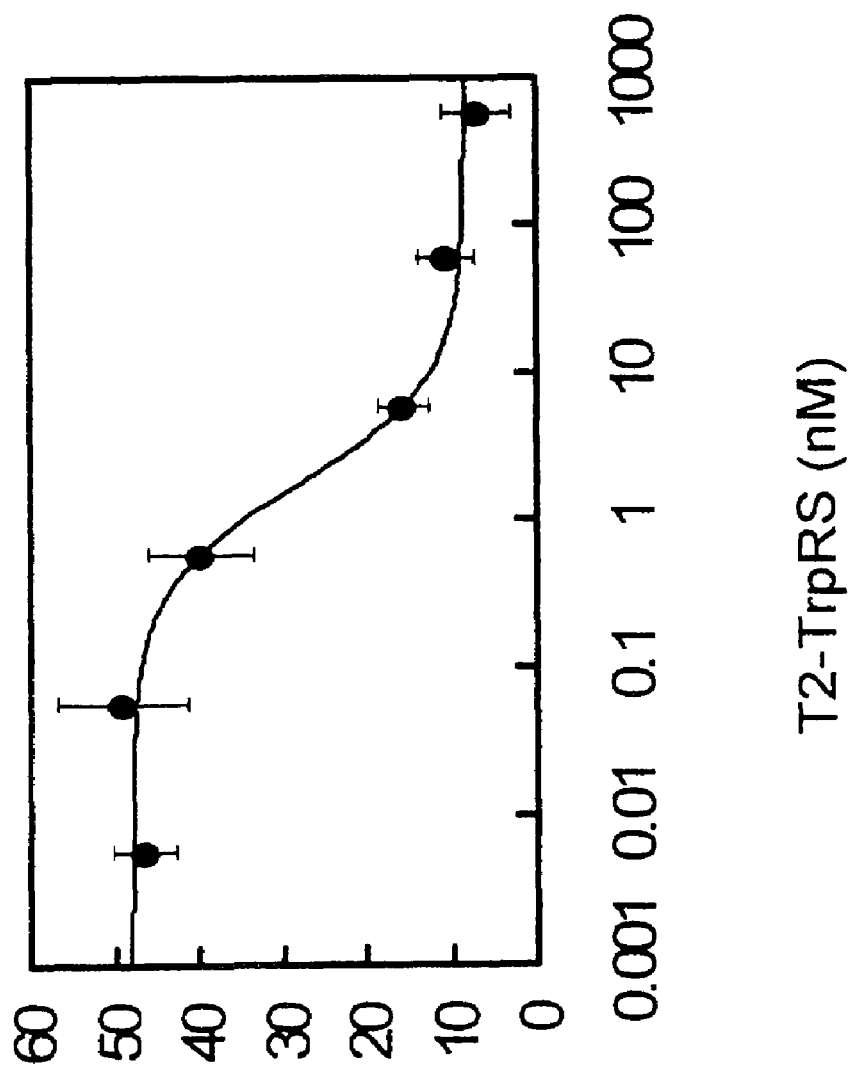
FIG. 4 is a graphical representation of data reported in Example 4, below.

Angiostatic Potency of T2 in the Mouse Matrigel Plug Assay. We examined T2 (SEQ ID NO: 7) to determine whether it had angiostatic activity, even though it had lost aminoacylation activity. The mouse matrigel assay was used to examine the angiostatic activity of T2 in vivo. $VEGF_{165}$-induces the development of blood vessels into the mouse matrigel plug. When T2 was added to the matrigel along with $VEGF_{165}$, angiogenesis was blocked in a dose-dependent manner with a $IC_{50}$ of 1.7 nM as shown in FIG. 4.

Figure 5:
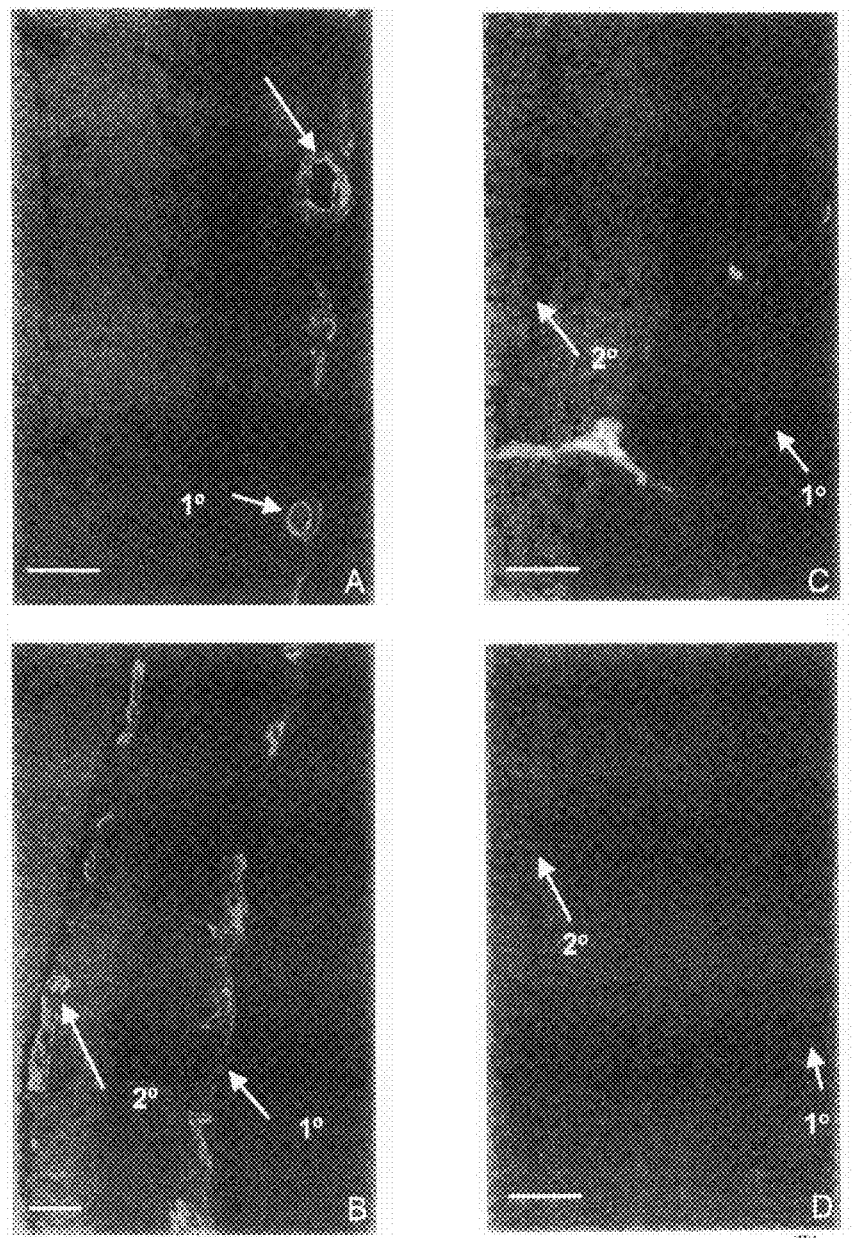
FIG. 5 shows a photomicrographs illustrating the binding localization of a fragment of TrpRS (T2) in the retina in a mouse model. The distribution of the injected protein was restricted to blood vessels as confirmed by co-staining labeled T2 treated eyes with an fluorescein-labeled (AL-EXA® 594) anti-collagen IV antibody. Panel A shows a retinal cross-section five days after injection of fluorescein-labeled T2 (on Day P12), the green fluorescence of the labeled T2 was still visible, indicated by the arrows; only a primary vascular layer (1°) was observed. Panel B shows that retinas injected on P7 with fluorescein-labeled full-length TrpRS developed a secondary vascular layer (2°) in addition to the primary layer (1°) by P12 but no vascular staining was observed. Panel C shows cross-sectioned slices of normal neonatal retinas stained with fluorescein-labeled T2; fluorescein-labeled T2 bound only to blood vessels within the primary and secondary vascular layers (indicated by the arrows). Panel D shows that no retinal vessel staining was observed when fluorescein-labeled full-length TrpRS was applied to the retinas in either the primary or the secondary vascular layers.

Fluorescein-labeled T2 Localizes to Retinal Blood Vessels. In order to visualize the intraocular localization of T2 (SEQ ID NO: 7), we examined the distribution of fluorescein-labeled T2 following intravitreous injection on postnatal day 7. Retinas were isolated the following day, sectioned and examined using confocal microscopy. The distribution of the injected protein was restricted to blood vessels. This localization was confirmed by co-staining labeled T2 treated eyes with an fluorescein-labeled (ALEXA® 594) anti-collagen IV antibody (data not shown). Five days after injection of fluorescein-labeled T2 (on P12), the green fluorescence of the labeled T2 was still visible (FIG. 5A). In these retinas, no secondary vascular layer was observed at P12, indicating that the fluorescein-labeled T2 retained angiostatic activity comparable to unlabeled T2. Retinas injected on P7 with fluorescein-labeled full-length TrpRS developed a secondary vascular layer by P12 but no vascular staining was observed (FIG. 5B). In FIG. 5, fluorescein-labeled proteins are green, collagen-labeled vessels are red, and nuclei are blue.

To further evaluate the binding properties of labeled T2, cross-sectioned slices of normal neonatal retinas were stained with fluorescein-labeled T2. Under these conditions, fluorescein-labeled T2 only bound to blood vessels (FIG. 5C). The binding was specific as it was blocked by pre-incubation with unlabeled T2 (data not shown). No retinal vessel staining was observed when fluorescein-labeled full-length TrpRS was applied to the retinas (FIG. 5D), consistent with the absence of angiostatic activity of the full-length enzyme.

As shown in FIG. 5, fluorescein-labeled T2 is angiostatic and localizes to retinal blood vessels. Fluorescein-labeled T2 (FIG. 5A) or full-length TrpRS (FIG. 5B) were injected (0.5 µl, intravitreous) on postnatal day 7 (P7). The retinas were harvested on P8 and stained with an anti-collagen IV antibody and DAPI nuclear stain, Labeled T2 (upper arrow pointing to vessel in FIG. 5A) localized to blood vessels in the primary superficial network (1°). Note that the secondary deep network is completely absent (2°). While both the primary (1°) and secondary (2°) vascular layers are present in eyes injected with fluorescein-labeled full-length TrpRS (arrows in FIG. 5B), no labeling is observed.

In a separate set of experiments, frozen sections of P15 retinas were stained with fluorescein-labeled T2 (FIG. 5C) or fluorescein-labeled full-length TrpRS (FIG. 5D) and imaged in the confocal scanning laser microscope. Labeled T2 selectively localized to blood vessels and appears as a bright green vessel penetrating the primary and secondary retinal vascular layers just below the label "2°" in FIG. 5C. No staining was observed with full-length TrpRS (FIG. 5D).

Full-length TrpRS contains a unique $NH_2$-terminal domain and lacks angiostatic activity. Removing part or all of this entire domain reveals a protein with angiostatic activity. The structures responsible for angiostatic activity of T2 appear to be contained within the core Rossmann fold nucleotide binding domain. The $NH_2$-terminal domain, which can be deleted by alternative splicing or by proteolysis, may regulate the angiostatic activity of TrpRS, possibly by revealing a binding site necessary for angiostasis that is inaccessible in full-length TrpRS.

VEGF-induced angiogenesis in the mouse matrigel model was completely inhibited by T2 as was physiological angiogenesis in the neonatal retina. Interestingly, the most potent anti-angiogenic effect of TrpRS fragments in vitro and in CAM and matrigel models is observed in VEGF-stimulated angiogenesis. The neonatal mouse retinal angiogenesis results are consistent with a link between VEGF-stimulated angiogenesis and the angiostatic effects of TrpRS fragments; retinal angiogenesis in this system may be driven by VEGF. In addition, the inhibition observed in the retinal model was specific for newly developing vessels; pre-existing (at the time of injection) primary vascular layer vessels were unaltered by the treatment. While the mechanism for the angiostatic activity of T2 is not known, the specific localization of T2 to the retinal endothelial vasculature and the selective effect of T2 on newly developing blood vessels suggest that T2 may function through an endothelial cell receptor expressed on proliferating or migrating cells. Further understanding of the mechanism of T2 angiostatic activity requires identification of the relevant cell receptor.

A variety of cell types that produce, upon interferon-γ stimulation, the angiostatic mini TrpRS also produce angiostatic factors such as IP-10. Thus, these results raise the possibility of a role for TrpRS in normal, physiologically relevant pathways of angiogenesis. Another ubiquitous cellular protein—pro-EMAPII (p43)—has two apparently unrelated roles similar to those reported here for TrpRS. Pro-EMAPII assists protein translation by associating with the multisynthetase complex of mammalian aminoacyl tRNA synthetases. It is processed and secreted as EMAPII, and a role for EMAPII as an angiostatic mediator during lung development has been suggested.

Thus, T2 can be utilized in physiologically relevant angiogenic remodeling observed under normal or pathological conditions. In normal angiogenesis, T2 can aid in establishing physiologically important avascular zones present in some organs such as the foveal avascular zone of the central retina. Pathological angiogenesis can occur if the cleavage of full-length TrpRS was inhibited, leading to an overgrowth of vessels.

In ocular diseases, neovascularization can lead to catastrophic loss of vision. These patients can potentially receive great benefit from therapeutic inhibition of angiogenesis. Vascular endothelial growth factor has been associated with neovascularization and macular edema in the retina, although it is believed that other angiogenic stimuli also have roles in retinal angiogenesis. We have observed an association between VEGF-stimulated angiogenesis and potent angiostatic activity of TrpRS fragments, making these molecules useful in the treatment of hypoxic, and other, proliferative retinopathies. There has been no report in the literature of an anti-angiogenic agent that completely inhibits angiogenesis 70% of the time, as does the T2 of the present invention (FIG. 5). Another advantage of TrpRS fragments is that they represent naturally occurring and, therefore, potentially non-immunogenic, anti-angiogenics. Thus, these molecules can be delivered via targeted cell- or viral vector-based therapy. Because many patients with neovascular eye diseases have associated systemic ischemic disease, local anti-angiogenic treatment with genetically engineered cells or viral vectors placed directly into the eye is desirable.

In addition to treatment of angiogenic retinopathies, the TrpRS fragments of the present invention, particularly T2 and angiogenesis inhibiting fragments thereof, can also inhibit solid tumor growth by preventing vascularization of the tumor. The TrpRS fragments of the present invention block VEGF-induced proliferation and chemotaxis of endothelial cells in vitro, and are thus useful in the treatment of any pathology involving unwanted endothelial cell proliferation and vascularization.

We claim:

1. An isolated nucleic acid encoding a tryptophanyl-t tRNA synthetase consisting of a nucleotide sequence encoding a water-soluble polypeptide fragment of human tryptophanyl-tRNA synthetase, the region of the nucleotide sequence encoding said fragment consisting of a nucleotide sequence that is at least 95 percent identical to the sequence of a polynucleotide selected from the group consisting of a polynucleotide of SEQ ID NO: 6, a polynucleotide that encodes the polypeptide consisting of SEQ ID NO: 7 and a polynucleotide that encodes a polypeptide consisting of SEQ ID NO: 12.

2. The isolated nucleic acid of claim 1, wherein the nucleic acid encodes a proprotein of the water-soluble polypeptide fragment of human tryptophanyl-tRNA synthetase, wherein the proprotein includes additional amino acid residues at the 5' terminus of the water-soluble polypeptide fragment of human tryptophanyl-tRNA synthetase.

3. The isolated nucleic acid of claim 2 further comprising a leader polynucleotide fused to the polynucleotide encoding the proprotein and in an open reading frame therewith, the leader polynucleotide encoding a secretory peptide sequence for controlling transport of the proprotein from a cell.

4. The isolated nucleic acid of claim 1 further comprising a leader polynucleotide fused to the polynucleotide encoding the water-soluble polypeptide fragment of human tryptophanyl-tRNA synthetase and in an open reading frame therewith, the leader polynucleotide encoding a secretory peptide sequence for controlling transport of the water-soluble polypeptide fragment of human tryptophanyl-tRNA synthetase from a cell.

5. A recombinant vector comprising a polynucleotide of claim 1.

6. A recombinant vector comprising a polynucleotide of claim 2.

7. A recombinant vector comprising a polynucleotide of claim 3.

8. A recombinant vector comprising a polynucleotide of claim 4.

9. A method of making a recombinant host cell comprising introducing a polynucleotide of claim 1 into a host cell.

10. A method of making a recombinant host cell comprising introducing a polynucleotide of claim 2 into a host cell.

11. A method of making a recombinant host cell comprising introducing a polynucleotide of claim 3 into a host cell.

12. A method of making a recombinant host cell comprising introducing a polynucleotide of claim 4 into a host cell.

13. A recombinant host cell which includes a polynucleotide of claim 1.

14. A recombinant host cell which includes a polynucleotide of claim 2.

15. A recombinant host cell which includes a polynucleotide of claim 3.

16. A recombinant host cell which includes a polynucleotide of claim 4.

17. A recombinant host cell of claim 13 that expresses the water-soluble polypeptide fragment of human tryptophanyl-tRNA synthetase.

18. A recombinant host cell of claim 14 that expresses the proprotein.

19. A recombinant host cell of claim 15 that expresses the proprotein.

20. A recombinant host cell of claim 16 that expresses the water-soluble polypeptide fragment of human tryptophanyl-tRNA synthetase.

* * * * *

SEQUENCE LISTING

```
<160> NUMBER OF SEQ ID NOS: 13

<210> SEQ ID NO 1
<211> LENGTH: 484
<212> TYPE: PRT
<213> ORGANISM: Artificial Sequence
<220> FEATURE:
<223> OTHER INFORMATION: Recombinant human trpRS

<400> SEQUENCE: 1

Met Pro Asn Ser Glu Pro Ala Ser Leu Leu Glu Leu Phe Asn Ser Ile
```

-continued

```
  1               5                   10                  15
Ala Thr Gln Gly Glu Leu Val Arg Ser Leu Lys Ala Gly Asn Ala Ser
             20                  25                  30
Lys Asp Glu Ile Asp Ser Ala Val Lys Met Leu Val Ser Leu Lys Met
             35                  40                  45
Ser Tyr Lys Ala Ala Ala Gly Glu Asp Tyr Lys Ala Asp Cys Pro Pro
             50                  55                  60
Gly Asn Pro Ala Pro Thr Ser Asn His Gly Pro Asp Ala Thr Glu Ala
 65                  70                  75                  80
Glu Glu Asp Phe Val Asp Pro Trp Thr Val Gln Thr Ser Ser Ala Lys
                 85                  90                  95
Gly Ile Asp Tyr Asp Lys Leu Ile Val Arg Phe Gly Ser Ser Lys Ile
                100                 105                 110
Asp Lys Glu Leu Ile Asn Arg Ile Glu Arg Ala Thr Gly Gln Arg Pro
            115                 120                 125
His His Phe Leu Arg Arg Gly Ile Phe Phe Ser His Arg Asp Met Asn
            130                 135                 140
Gln Val Leu Asp Ala Tyr Glu Asn Lys Lys Pro Phe Tyr Leu Tyr Thr
145                 150                 155                 160
Gly Arg Gly Pro Ser Ser Glu Ala Met His Val Gly His Leu Ile Pro
                165                 170                 175
Phe Ile Phe Thr Lys Trp Leu Gln Asp Val Phe Asn Val Pro Leu Val
                180                 185                 190
Ile Gln Met Thr Asp Asp Glu Lys Tyr Leu Trp Lys Asp Leu Thr Leu
            195                 200                 205
Asp Gln Ala Tyr Gly Asp Ala Val Glu Asn Ala Lys Asp Ile Ile Ala
            210                 215                 220
Cys Gly Phe Asp Ile Asn Lys Thr Phe Ile Phe Ser Asp Leu Asp Tyr
225                 230                 235                 240
Met Gly Met Ser Ser Gly Phe Tyr Lys Asn Val Val Lys Ile Gln Lys
                245                 250                 255
His Val Thr Phe Asn Gln Val Lys Gly Ile Phe Gly Phe Thr Asp Ser
                260                 265                 270
Asp Cys Ile Gly Lys Ile Ser Phe Pro Ala Ile Gln Ala Ala Pro Ser
            275                 280                 285
Phe Ser Asn Ser Phe Pro Gln Ile Phe Arg Asp Arg Thr Asp Ile Gln
            290                 295                 300
Cys Leu Ile Pro Cys Ala Ile Asp Gln Asp Pro Tyr Phe Arg Met Thr
305                 310                 315                 320
Arg Asp Val Ala Pro Arg Ile Gly Tyr Pro Lys Pro Ala Leu Leu His
                325                 330                 335
Ser Thr Phe Phe Pro Ala Leu Gln Gly Ala Gln Thr Lys Met Ser Ala
                340                 345                 350
Ser Asp Pro Asn Ser Ser Ile Phe Leu Thr Asp Thr Ala Lys Gln Ile
            355                 360                 365
Lys Thr Lys Val Asn Lys His Ala Phe Ser Gly Gly Arg Asp Thr Ile
            370                 375                 380
Glu Glu His Arg Gln Phe Gly Gly Asn Cys Asp Val Asp Val Ser Phe
385                 390                 395                 400
Met Tyr Leu Thr Phe Phe Leu Glu Asp Asp Lys Leu Glu Gln Ile
                405                 410                 415
Arg Lys Asp Tyr Thr Ser Gly Ala Met Leu Thr Gly Glu Leu Lys Lys
            420                 425                 430
```

```
Ala Leu Ile Glu Val Leu Gln Pro Leu Ile Ala Glu His Gln Ala Arg
        435                 440                 445

Arg Lys Glu Val Thr Asp Glu Ile Val Lys Glu Phe Met Thr Pro Arg
    450                 455                 460

Lys Leu Ser Phe Asp Phe Gln Lys Leu Ala Ala Ala Leu Glu His His
465                 470                 475                 480

His His His His

<210> SEQ ID NO 2
<211> LENGTH: 4877
<212> TYPE: DNA
<213> ORGANISM: Artificial Sequence
<220> FEATURE:
<223> OTHER INFORMATION: Recombinant human mini-TrpRS in pET20B
<220> FEATURE:
<221> NAME/KEY: CDS
<222> LOCATION: (3428)...(4738)

<400> SEQUENCE: 2
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct tgacgttgg agtccacgtt      300 ctttaatagt ggactcttgt tccaaactgg aacaacactc aaccctatct cggtctattc     360
ttttgattta aagggatttt gccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt      660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg atcatgtaa ctcgccttga     1080 tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc cttttttgata atctcatgac    1560 caaaatccct taacgtgagt tttcgttcca ctgagcgtca gaccccgtag aaaagatcaa    1620
```

```
aggatcttct tgagatccttt tttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
ctttcctgcg ttatccctg  attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg  atttctgttc atggggtaa     2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360
tatagggaga ccacaacggt ttccctctag aaataatttt gtttaacttt aagaaggaga    3420 tatacat atg agc tac aaa gct gcc gcg ggg gag gat tac aag gct gac    3469
        Met Ser Tyr Lys Ala Ala Ala Gly Glu Asp Tyr Lys Ala Asp
        1               5                  10 tgt cct cca ggg aac cca gca cct acc agt aat cat ggc cca gat gcc    3517
Cys Pro Pro Gly Asn Pro Ala Pro Thr Ser Asn His Gly Pro Asp Ala
 15                  20                  25                  30 aca gaa gct gaa gag gat ttt gtg gac cca tgg aca gta cag aca agc    3565
Thr Glu Ala Glu Glu Asp Phe Val Asp Pro Trp Thr Val Gln Thr Ser
                 35                  40                  45 agt gca aaa ggc ata gac tac gat aag ctc att gtt cgg ttt gga agt    3613
Ser Ala Lys Gly Ile Asp Tyr Asp Lys Leu Ile Val Arg Phe Gly Ser
             50                  55                  60 agt aaa att gac aaa gag cta ata aac cga ata gag aga gcc acc ggc    3661
Ser Lys Ile Asp Lys Glu Leu Ile Asn Arg Ile Glu Arg Ala Thr Gly
 65                  70                  75
```

|  |  |
|---|---:|
| caa aga cca cac cac ttc ctg cgc aga ggc atc ttc ttc tca cac aga<br>Gln Arg Pro His His Phe Leu Arg Arg Gly Ile Phe Phe Ser His Arg<br>    80                      85                      90 | 3709 |
| gat atg aat cag gtt ctt gat gcc tat gaa aat aag aag cca ttt tat<br>Asp Met Asn Gln Val Leu Asp Ala Tyr Glu Asn Lys Lys Pro Phe Tyr<br>95                   100                 105              110 | 3757 |
| ctg tac acg ggc cgg ggc ccc tct tct gaa gca atg cat gta ggt cac<br>Leu Tyr Thr Gly Arg Gly Pro Ser Ser Glu Ala Met His Val Gly His<br>                115                 120              125 | 3805 |
| ctc att cca ttt att ttc aca aag tgg ctc cag gat gta ttt aac gtg<br>Leu Ile Pro Phe Ile Phe Thr Lys Trp Leu Gln Asp Val Phe Asn Val<br>            130                 135              140 | 3853 |
| ccc ttg gtc atc cag atg acg gat gac gag aag tat ctg tgg aag gac<br>Pro Leu Val Ile Gln Met Thr Asp Asp Glu Lys Tyr Leu Trp Lys Asp<br>        145                 150              155 | 3901 |
| ctg acc ctg gac cag gcc tat ggc gat gct gtt gag aat gcc aag gac<br>Leu Thr Leu Asp Gln Ala Tyr Gly Asp Ala Val Glu Asn Ala Lys Asp<br>160                 165              170 | 3949 |
| atc atc gcc tgt ggc ttt gac atc aac aag act ttc ata ttc tct gac<br>Ile Ile Ala Cys Gly Phe Asp Ile Asn Lys Thr Phe Ile Phe Ser Asp<br>175                180               185              190 | 3997 |
| ctg gac tac atg ggg atg agc tca ggt ttc tac aaa aat gtg gtg aag<br>Leu Asp Tyr Met Gly Met Ser Ser Gly Phe Tyr Lys Asn Val Val Lys<br>                195               200              205 | 4045 |
| att caa aag cat gtt acc ttc aac caa gtg aaa ggc att ttc ggc ttc<br>Ile Gln Lys His Val Thr Phe Asn Gln Val Lys Gly Ile Phe Gly Phe<br>            210               215              220 | 4093 |
| act gac agc gac tgc att ggg aag atc agt ttt cct gcc atc cag gct<br>Thr Asp Ser Asp Cys Ile Gly Lys Ile Ser Phe Pro Ala Ile Gln Ala<br>        225               230              235 | 4141 |
| gct ccc tcc ttc agc aac tca ttc cca cag atc ttc cga gac agg acg<br>Ala Pro Ser Phe Ser Asn Ser Phe Pro Gln Ile Phe Arg Asp Arg Thr<br>240                 245              250 | 4189 |
| gat atc cag tgc ctt atc cca tgt gcc att gac cag gat cct tac ttt<br>Asp Ile Gln Cys Leu Ile Pro Cys Ala Ile Asp Gln Asp Pro Tyr Phe<br>255                 260               265              270 | 4237 |
| aga atg aca agg gac gtc gcc ccc agg atc ggc tat cct aaa cca gcc<br>Arg Met Thr Arg Asp Val Ala Pro Arg Ile Gly Tyr Pro Lys Pro Ala<br>            275               280              285 | 4285 |
| ctg ttg cac tcc acc ttc ttc cca gcc ctg cag ggc gcc cag acc aaa<br>Leu Leu His Ser Thr Phe Phe Pro Ala Leu Gln Gly Ala Gln Thr Lys<br>            290               295              300 | 4333 |
| atg agt gcc agc gac cca aac tcc tcc atc ttc ctc acc gac acg gcc<br>Met Ser Ala Ser Asp Pro Asn Ser Ser Ile Phe Leu Thr Asp Thr Ala<br>        305               310              315 | 4381 |
| aag cag atc aaa acc aag gtc aat aag cat gcg ttt tct gga ggg aga<br>Lys Gln Ile Lys Thr Lys Val Asn Lys His Ala Phe Ser Gly Gly Arg<br>320                 325               330 | 4429 |
| gac acc atc gag gag cac agg cag ttt ggg ggc aac tgt gat gtg gac<br>Asp Thr Ile Glu Glu His Arg Gln Phe Gly Gly Asn Cys Asp Val Asp<br>335                 340               345              350 | 4477 |
| gtg tct ttc atg tac ctg acc ttc ttc ctc gag gac gac gac aag ctc<br>Val Ser Phe Met Tyr Leu Thr Phe Phe Leu Glu Asp Asp Asp Lys Leu<br>                355               360              365 | 4525 |
| gag cag atc agg aag gat tac acc agc gga gcc atg ctc acc ggt gag<br>Glu Gln Ile Arg Lys Asp Tyr Thr Ser Gly Ala Met Leu Thr Gly Glu<br>            370               375              380 | 4573 |
| ctc aag aag gca ctc ata gag gtt ctg cag ccc ttg atc gca gag cac<br>Leu Lys Lys Ala Leu Ile Glu Val Leu Gln Pro Leu Ile Ala Glu His | 4621 |

-continued

```
                    385                 390                 395
cag gcc cgg cgc aag gag gtc acg gat gag ata gtg aaa gag ttc atg    4669
Gln Ala Arg Arg Lys Glu Val Thr Asp Glu Ile Val Lys Glu Phe Met
    400                 405                 410 act ccc cgg aag ctg tcc ttc gac ttt cag aag ctt gcg gcc gca ctc    4717
Thr Pro Arg Lys Leu Ser Phe Asp Phe Gln Lys Leu Ala Ala Ala Leu
415                 420                 425                 430 gag cac cac cac cac cac cac tgagatccgg ctgctaacaa agcccgaaag       4768
Glu His His His His His His
            435 gaagctgagt tggctgctgc caccgctgag caataactag cataacccct tggggcctct  4828 aaacgggtct tgaggggttt tttgctgaaa ggaggaacta tatccggat              4877

<210> SEQ ID NO 3
<211> LENGTH: 437
<212> TYPE: PRT
<213> ORGANISM: Artificial Sequence
<220> FEATURE:
<223> OTHER INFORMATION: human mini TrpRS in pET20B

<400> SEQUENCE: 3

Met Ser Tyr Lys Ala Ala Ala Gly Glu Asp Tyr Lys Ala Asp Cys Pro
 1               5                  10                  15

Pro Gly Asn Pro Ala Pro Thr Ser Asn His Gly Pro Asp Ala Thr Glu
            20                  25                  30

Ala Glu Glu Asp Phe Val Asp Pro Trp Thr Val Gln Thr Ser Ser Ala
        35                  40                  45

Lys Gly Ile Asp Tyr Asp Lys Leu Ile Val Arg Phe Gly Ser Ser Lys
    50                  55                  60

Ile Asp Lys Glu Leu Ile Asn Arg Ile Glu Arg Ala Thr Gly Gln Arg
65                  70                  75                  80

Pro His His Phe Leu Arg Arg Gly Ile Phe Phe Ser His Arg Asp Met
                85                  90                  95

Asn Gln Val Leu Asp Ala Tyr Glu Asn Lys Lys Pro Phe Tyr Leu Tyr
            100                 105                 110

Thr Gly Arg Gly Pro Ser Ser Glu Ala Met His Val Gly His Leu Ile
        115                 120                 125

Pro Phe Ile Phe Thr Lys Trp Leu Gln Asp Val Phe Asn Val Pro Leu
    130                 135                 140

Val Ile Gln Met Thr Asp Asp Glu Lys Tyr Leu Trp Lys Asp Leu Thr
145                 150                 155                 160

Leu Asp Gln Ala Tyr Gly Asp Ala Val Glu Asn Ala Lys Asp Ile Ile
                165                 170                 175

Ala Cys Gly Phe Asp Ile Asn Lys Thr Phe Ile Phe Ser Asp Leu Asp
            180                 185                 190

Tyr Met Gly Met Ser Ser Gly Phe Tyr Lys Asn Val Val Lys Ile Gln
        195                 200                 205

Lys His Val Thr Phe Asn Gln Val Lys Gly Ile Phe Gly Phe Thr Asp
    210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                245                 250                 255

Gln Cys Leu Ile Pro Cys Ala Ile Asp Gln Asp Pro Tyr Phe Arg Met
            260                 265                 270
```

```
Thr Arg Asp Val Ala Pro Arg Ile Gly Tyr Pro Lys Pro Ala Leu Leu
        275                 280                 285

His Ser Thr Phe Phe Pro Ala Leu Gln Gly Ala Gln Thr Lys Met Ser
        290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu Glu His Arg Gln Phe Gly Gly Asn Cys Asp Val Asp Val Ser
            340                 345                 350

Phe Met Tyr Leu Thr Phe Phe Leu Glu Asp Asp Lys Leu Glu Gln
        355                 360                 365

Ile Arg Lys Asp Tyr Thr Ser Gly Ala Met Leu Thr Gly Glu Leu Lys
    370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln Lys Leu Ala Ala Ala Leu Glu His
            420                 425                 430

His His His His His
        435
```

```
<210> SEQ ID NO 4
<211> LENGTH: 4811
<212> TYPE: DNA
<213> ORGANISM: Artificial Sequence
<220> FEATURE:
<223> OTHER INFORMATION: Cleavage Product T1 of recombinant human TrpRS
<220> FEATURE:
<221> NAME/KEY: CDS
<222> LOCATION: (3428)...(4672)

<400> SEQUENCE: 4
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg       180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aacccatctc ggtctattc      360 ttttgattta agggatttt gccgatttc ggcctattgg ttaaaaaatg agctgattta       420
acaaaaattt aacgcgaatt ttaacaaaat attaacgttt acaatttcag gtggcacttt     480
tcggggaaat gtgcgcggaa ccctatttg tttattttc taaatacatt caaatatgta       540
tccgctcatg agacaataac cctgataaat gcttcaataa tattgaaaaa ggaagagtat     600
gagtattcaa catttccgtg tcgcccttat ccctttttt gcggcatttt gccttcctgt      660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcactttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
```

```
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct aacgtgagt tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360
```

-continued

```
tatagggaga ccacaacggt ttccctctag aaataatttt gtttaacttt aagaaggaga      3420 tatacat atg agt aat cat ggc cca gat gcc aca gaa gct gaa gag gat        3469
        Met Ser Asn His Gly Pro Asp Ala Thr Glu Ala Glu Glu Asp
        1               5                   10 ttt gtg gac cca tgg aca gta cag aca agc agt gca aaa ggc ata gac        3517
Phe Val Asp Pro Trp Thr Val Gln Thr Ser Ser Ala Lys Gly Ile Asp
15                  20                  25                  30 tac gat aag ctc att gtt cgg ttt gga agt agt aaa att gac aaa gag        3565
Tyr Asp Lys Leu Ile Val Arg Phe Gly Ser Ser Lys Ile Asp Lys Glu
                35                  40                  45 cta ata aac cga ata gag aga gcc acc ggc caa aga cca cac cac ttc        3613
Leu Ile Asn Arg Ile Glu Arg Ala Thr Gly Gln Arg Pro His His Phe
        50                  55                  60 ctg cgc aga ggc atc ttc ttc tca cac aga gat atg aat cag gtt ctt        3661
Leu Arg Arg Gly Ile Phe Phe Ser His Arg Asp Met Asn Gln Val Leu
            65                  70                  75 gat gcc tat gaa aat aag aag cca ttt tat ctg tac acg ggc cgg ggc        3709
Asp Ala Tyr Glu Asn Lys Lys Pro Phe Tyr Leu Tyr Thr Gly Arg Gly
    80                  85                  90 ccc tct tct gaa gca atg cat gta ggt cac ctc att cca ttt att ttc        3757
Pro Ser Ser Glu Ala Met His Val Gly His Leu Ile Pro Phe Ile Phe
95                  100                 105                 110 aca aag tgg ctc cag gat gta ttt aac gtg ccc ttg gtc atc cag atg        3805
Thr Lys Trp Leu Gln Asp Val Phe Asn Val Pro Leu Val Ile Gln Met
                115                 120                 125 acg gat gac gag aag tat ctg tgg aag gac ctg acc ctg gac cag gcc        3853
Thr Asp Asp Glu Lys Tyr Leu Trp Lys Asp Leu Thr Leu Asp Gln Ala
            130                 135                 140 tat ggc gat gct gtt gag aat gcc aag gac atc atc gcc tgt ggc ttt        3901
Tyr Gly Asp Ala Val Glu Asn Ala Lys Asp Ile Ile Ala Cys Gly Phe
        145                 150                 155 gac atc aac aag act ttc ata ttc tct gac ctg gac tac atg ggg atg        3949
Asp Ile Asn Lys Thr Phe Ile Phe Ser Asp Leu Asp Tyr Met Gly Met
    160                 165                 170 agc tca ggt ttc tac aaa aat gtg gtg aag att caa aag cat gtt acc        3997
Ser Ser Gly Phe Tyr Lys Asn Val Val Lys Ile Gln Lys His Val Thr
175                 180                 185                 190 ttc aac caa gtg aaa ggc att ttc ggc ttc act gac agc gac tgc att        4045
Phe Asn Gln Val Lys Gly Ile Phe Gly Phe Thr Asp Ser Asp Cys Ile
                195                 200                 205 ggg aag atc agt ttt cct gcc atc cag gct gct ccc tcc ttc agc aac        4093
Gly Lys Ile Ser Phe Pro Ala Ile Gln Ala Ala Pro Ser Phe Ser Asn
            210                 215                 220 tca ttc cca cag atc ttc cga gac agg acg gat atc cag tgc ctt atc        4141
Ser Phe Pro Gln Ile Phe Arg Asp Arg Thr Asp Ile Gln Cys Leu Ile
        225                 230                 235 cca tgt gcc att gac cag gat cct tac ttt aga atg aca agg gac gtc        4189
Pro Cys Ala Ile Asp Gln Asp Pro Tyr Phe Arg Met Thr Arg Asp Val
240                 245                 250 gcc ccc agg atc ggc tat cct aaa cca gcc ctg ttg cac tcc acc ttc        4237
Ala Pro Arg Ile Gly Tyr Pro Lys Pro Ala Leu Leu His Ser Thr Phe
255                 260                 265                 270 ttc cca gcc ctg cag ggc gcc cag acc aaa atg agt gcc agc gac cca        4285
Phe Pro Ala Leu Gln Gly Ala Gln Thr Lys Met Ser Ala Ser Asp Pro
                275                 280                 285 aac tcc tcc atc ttc ctc acc gac acg gcc aag cag atc aaa acc aag        4333
Asn Ser Ser Ile Phe Leu Thr Asp Thr Ala Lys Gln Ile Lys Thr Lys
            290                 295                 300 gtc aat aag cat gcg ttt tct gga ggg aga gac acc atc gag gag cac        4381
Val Asn Lys His Ala Phe Ser Gly Gly Arg Asp Thr Ile Glu Glu His
```

-continued

```
Val Asn Lys His Ala Phe Ser Gly Gly Arg Asp Thr Ile Glu Glu His
        305                 310                 315 agg cag ttt ggg ggc aac tgt gat gtg gac gtg tct ttc atg tac ctg    4429
Arg Gln Phe Gly Gly Asn Cys Asp Val Asp Val Ser Phe Met Tyr Leu
320                 325                 330 acc ttc ttc ctc gag gac gac gac aag ctc gag cag atc agg aag gat    4477
Thr Phe Phe Leu Glu Asp Asp Asp Lys Leu Glu Gln Ile Arg Lys Asp
335                 340                 345                 350 tac acc agc gga gcc atg ctc acc ggt gag ctc aag aag gca ctc ata    4525
Tyr Thr Ser Gly Ala Met Leu Thr Gly Glu Leu Lys Lys Ala Leu Ile
            355                 360                 365 gag gtt ctg cag ccc ttg atc gca gag cac cag gcc cgg cgc aag gag    4573
Glu Val Leu Gln Pro Leu Ile Ala Glu His Gln Ala Arg Arg Lys Glu
        370                 375                 380 gtc acg gat gag ata gtg aaa gag ttc atg act ccc cgg aag ctg tcc    4621
Val Thr Asp Glu Ile Val Lys Glu Phe Met Thr Pro Arg Lys Leu Ser
385                 390                 395 ttc gac ttt cag aag ctt gcg gcc gca ctc gag cac cac cac cac cac    4669
Phe Asp Phe Gln Lys Leu Ala Ala Ala Leu Glu His His His His His
400                 405                 410 cac tgagatccgg ctgctaacaa agcccgaaag gaagctgagt tggctgctgc         4722
His
415 caccgctgag caataactag cataacccct tggggcctct aaacgggtct tgaggggttt   4782 tttgctgaaa ggaggaacta tatccggat                                    4811

<210> SEQ ID NO 5
<211> LENGTH: 415
<212> TYPE: PRT
<213> ORGANISM: Artificial Sequence
<220> FEATURE:
<223> OTHER INFORMATION: Cleavage Product T1 of recombinant human TrpRS

<400> SEQUENCE: 5

Met Ser Asn His Gly Pro Asp Ala Thr Glu Ala Glu Asp Phe Val
1               5                   10                  15

Asp Pro Trp Thr Val Gln Thr Ser Ser Ala Lys Gly Ile Asp Tyr Asp
            20                  25                  30

Lys Leu Ile Val Arg Phe Gly Ser Ser Lys Ile Asp Lys Glu Leu Ile
        35                  40                  45

Asn Arg Ile Glu Arg Ala Thr Gly Gln Arg Pro His His Phe Leu Arg
    50                  55                  60

Arg Gly Ile Phe Phe Ser His Arg Asp Met Asn Gln Val Leu Asp Ala
65                  70                  75                  80

Tyr Glu Asn Lys Lys Pro Phe Tyr Leu Tyr Thr Gly Arg Gly Pro Ser
                85                  90                  95

Ser Glu Ala Met His Val Gly His Leu Ile Pro Phe Ile Phe Thr Lys
            100                 105                 110

Trp Leu Gln Asp Val Phe Asn Val Pro Leu Val Ile Gln Met Thr Asp
        115                 120                 125

Asp Glu Lys Tyr Leu Trp Lys Asp Leu Thr Leu Asp Gln Ala Tyr Gly
    130                 135                 140

Asp Ala Val Glu Asn Ala Lys Asp Ile Ile Ala Cys Gly Phe Asp Ile
145                 150                 155                 160

Asn Lys Thr Phe Ile Phe Ser Asp Leu Asp Tyr Met Gly Met Ser Ser
                165                 170                 175

Gly Phe Tyr Lys Asn Val Val Lys Ile Gln Lys His Val Thr Phe Asn
```

|   |   |   | 180 |   |   |   | 185 |   |   |   | 190 |
|---|---|---|---|---|---|---|---|---|---|---|---|

Gln Val Lys Gly Ile Phe Gly Phe Thr Asp Ser Asp Cys Ile Gly Lys
        195              200              205

Ile Ser Phe Pro Ala Ile Gln Ala Ala Pro Ser Phe Ser Asn Ser Phe
  210               215              220

Pro Gln Ile Phe Arg Asp Arg Thr Asp Ile Gln Cys Leu Ile Pro Cys
225               230              235              240

Ala Ile Asp Gln Asp Pro Tyr Phe Arg Met Thr Arg Asp Val Ala Pro
        245              250              255

Arg Ile Gly Tyr Pro Lys Pro Ala Leu Leu His Ser Thr Phe Phe Pro
          260              265              270

Ala Leu Gln Gly Ala Gln Thr Lys Met Ser Ala Ser Asp Pro Asn Ser
  275               280              285

Ser Ile Phe Leu Thr Asp Thr Ala Lys Gln Ile Lys Thr Lys Val Asn
        290              295              300

Lys His Ala Phe Ser Gly Gly Arg Asp Thr Ile Glu Glu His Arg Gln
305               310              315              320

Phe Gly Gly Asn Cys Asp Val Asp Val Ser Phe Met Tyr Leu Thr Phe
          325              330              335

Phe Leu Glu Asp Asp Asp Lys Leu Glu Gln Ile Arg Lys Asp Tyr Thr
        340              345              350

Ser Gly Ala Met Leu Thr Gly Glu Leu Lys Lys Ala Leu Ile Glu Val
          355              360              365

Leu Gln Pro Leu Ile Ala Glu His Gln Ala Arg Arg Lys Glu Val Thr
  370               375              380

Asp Glu Ile Val Lys Glu Phe Met Thr Pro Arg Lys Leu Ser Phe Asp
385               390              395              400

Phe Gln Lys Leu Ala Ala Ala Leu Glu His His His His His
        405              410              415

<210> SEQ ID NO 6
<211> LENGTH: 4742
<212> TYPE: DNA
<213> ORGANISM: Artificial Sequence
<220> FEATURE:
<223> OTHER INFORMATION: Cleavage Product T2 of recombinant human TrpRS
<220> FEATURE:
<221> NAME/KEY: CDS
<222> LOCATION: (3428)...(4603)

<400> SEQUENCE: 6

| | | |
|---|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta tagggatttt gccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg agacaataac cctgataaat gcttcaataa tattgaaaaa ggaagagtat | 600 |
| gagtattcaa catttccgtg tcgcccttat tccctttttt gcggcatttt gccttcctgt | 660 |

```
ttttgctcac ccagaaacgc tggtgaaagt aaaagatgct gaagatcagt tgggtgcacg   720
agtgggttac atcgaactgg atctcaacag cggtaagatc cttgagagtt ttcgccccga   780
agaacgtttt ccaatgatga gcactttaaa agttctgcta tgtggcgcgg tattatcccg   840
tattgacgcc gggcaagagc aactcggtcg ccgcatacac tattctcaga atgacttggt   900
tgagtactca ccagtcacag aaaagcatct tacggatggc atgacagtaa gagaattatg   960
cagtgctgcc ataaccatga gtgataacac tgcggccaac ttacttctga caacgatcgg  1020
aggaccgaag gagctaaccg cttttttgca caacatgggg gatcatgtaa ctcgccttga  1080
tcgttgggaa ccgagctga atgaagccat accaaacgac gagcgtgaca ccacgatgcc  1140
tgcagcaatg gcaacaacgt tgcgcaaact attaactggc gaactactta ctctagcttc  1200
ccggcaacaa ttaatagact ggatggaggc ggataaagtt gcaggaccac ttctgcgctc  1260
ggcccttccg gctggctggt ttattgctga taaatctgga gccggtgagc gtgggtctcg  1320
cggtatcatt gcagcactgg ggccagatgg taagccctcc cgtatcgtag ttatctacac  1380
gacggggagt caggcaacta tggatgaacg aaatagacag atcgctgaga taggtgcctc  1440
actgattaag cattggtaac tgtcagacca agtttactca tatatacttt agattgattt  1500
aaaacttcat ttttaattta aaaggatcta ggtgaagatc ctttttgata atctcatgac  1560
caaaatccct taacgtgagt tttcgttcca ctgagcgtca gaccccgtag aaaagatcaa  1620
aggatcttct tgagatcctt ttttttctgcg cgtaatctgc tgcttgcaaa caaaaaaacc  1680
accgctacca gcggtggttt gtttgccgga tcaagagcta ccaactcttt ttccgaaggt  1740
aactggcttc agcagagcgc agataccaaa tactgtcctt ctagtgtagc cgtagttagg  1800
ccaccacttc aagaactctg tagcaccgcc tacatacctc gctctgctaa tcctgttacc  1860
agtggctgct gccagtggcg ataagtcgtg tcttaccggg ttggactcaa gacgatagtt  1920
accggataag cgcagcggt cgggctgaac ggggggttcg tgcacacagc ccagcttgga  1980
gcgaacgacc tacaccgaac tgagatacct acagcgtgag ctatgagaaa gcgccacgct  2040
tcccgaaggg agaaaggcgg acaggtatcc ggtaagcggc agggtcggaa caggagagcg  2100
cacgagggag cttccagggg gaaacgcctg gtatctttat agtcctgtcg ggtttcgcca  2160
cctctgactt gagcgtcgat ttttgtgatg ctcgtcaggg gggcggagcc tatgaaaaaa  2220
cgccagcaac gcggcctttt tacggttcct ggccttttgc tggccttttg ctcacatgtt  2280
ctttcctgcg ttatcccctg attctgtgga taaccgtatt accgcctttg agtgagctga  2340
taccgctcgc cgcagccgaa cgaccgagcg cagcgagtca gtgagcgagg aagcggaaga  2400
gcgcctgatg cggtattttc tccttacgca tctgtgcggt atttcacacc gcatatatgg  2460
tgcactctca gtacaatctg ctctgatgcc gcatagttaa gccagtatac actccgctat  2520
cgctacgtga ctgggtcatg gctgcgcccc gacacccgcc aacacccgct gacgcgccct  2580
gacgggcttg tctgctcccg gcatccgctt acagacaagc tgtgaccgtc tccgggagct  2640
gcatgtgtca gaggttttca ccgtcatcac cgaaacgcgc gaggcagctg cggtaaagct  2700
catcagcgtg gtcgtgaagc gattcacaga tgtctgcctg ttcatccgcg tccagctcgt  2760
tgagtttctc cagaagcgtt aatgtctggc ttctgataaa gcgggccatg ttaagggcgg  2820
ttttttcctg tttggtcact gatgcctccg tgtaaggggg atttctgttc atgggggtaa  2880
tgataccgat gaaacgagag aggatgctca cgatacgggt tactgatgat gaacatgccc  2940
ggttactgga acgttgtgag ggtaaacaac tggcggtatg gatgcggcgg gaccagagaa  3000
aaatcactca gggtcaatgc cagcgcttcg ttaatacaga tgtaggtgtt ccacagggta  3060
```

-continued

```
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360 tataggga ga ccacaacggt ttccctctag aaataatttt gtttaacttt aagaaggaga   3420
```

| | | | | | | | | | | | | | | | | |
|---|---|---|---|---|---|---|---|---|---|---|---|---|---|---|---|---|
| tatacat | atg | agt | gca | aaa | ggc | ata | gac | tac | gat | aag | ctc | att | gtt | cgg | | 3469 |
| | Met | Ser | Ala | Lys | Gly | Ile | Asp | Tyr | Asp | Lys | Leu | Ile | Val | Arg | | |
| | 1 | | | 5 | | | | | 10 | | | | | | | |
| ttt | gga | agt | agt | aaa | att | gac | aaa | gag | cta | ata | aac | cga | ata | gag | aga | 3517 |
| Phe | Gly | Ser | Ser | Lys | Ile | Asp | Lys | Glu | Leu | Ile | Asn | Arg | Ile | Glu | Arg | |
| 15 | | | | 20 | | | | | 25 | | | | | 30 | | |
| gcc | acc | ggc | caa | aga | cca | cac | cac | ttc | ctg | cgc | aga | ggc | atc | ttc | ttc | 3565 |
| Ala | Thr | Gly | Gln | Arg | Pro | His | His | Phe | Leu | Arg | Arg | Gly | Ile | Phe | Phe | |
| | | | 35 | | | | | 40 | | | | | 45 | | | |
| tca | cac | aga | gat | atg | aat | cag | gtt | ctt | gat | gcc | tat | gaa | aat | aag | aag | 3613 |
| Ser | His | Arg | Asp | Met | Asn | Gln | Val | Leu | Asp | Ala | Tyr | Glu | Asn | Lys | Lys | |
| | | | 50 | | | | | 55 | | | | | 60 | | | |
| cca | ttt | tat | ctg | tac | acg | ggc | cgg | ggc | ccc | tct | tct | gaa | gca | atg | cat | 3661 |
| Pro | Phe | Tyr | Leu | Tyr | Thr | Gly | Arg | Gly | Pro | Ser | Ser | Glu | Ala | Met | His | |
| | | 65 | | | | | 70 | | | | | 75 | | | | |
| gta | ggt | cac | ctc | att | cca | ttt | att | ttc | aca | aag | tgg | ctc | cag | gat | gta | 3709 |
| Val | Gly | His | Leu | Ile | Pro | Phe | Ile | Phe | Thr | Lys | Trp | Leu | Gln | Asp | Val | |
| | 80 | | | | | 85 | | | | | 90 | | | | | |
| ttt | aac | gtg | ccc | ttg | gtc | atc | cag | atg | acg | gat | gac | gag | aag | tat | ctg | 3757 |
| Phe | Asn | Val | Pro | Leu | Val | Ile | Gln | Met | Thr | Asp | Asp | Glu | Lys | Tyr | Leu | |
| 95 | | | | 100 | | | | | 105 | | | | | 110 | | |
| tgg | aag | gac | ctg | acc | ctg | gac | cag | gcc | tat | ggc | gat | gct | gtt | gag | aat | 3805 |
| Trp | Lys | Asp | Leu | Thr | Leu | Asp | Gln | Ala | Tyr | Gly | Asp | Ala | Val | Glu | Asn | |
| | | | 115 | | | | | 120 | | | | | 125 | | | |
| gcc | aag | gac | atc | atc | gcc | tgt | ggc | ttt | gac | atc | aac | aag | act | ttc | ata | 3853 |
| Ala | Lys | Asp | Ile | Ile | Ala | Cys | Gly | Phe | Asp | Ile | Asn | Lys | Thr | Phe | Ile | |
| | | | 130 | | | | | 135 | | | | | 140 | | | |
| ttc | tct | gac | ctg | gac | tac | atg | ggg | atg | agc | tca | ggt | ttc | tac | aaa | aat | 3901 |
| Phe | Ser | Asp | Leu | Asp | Tyr | Met | Gly | Met | Ser | Ser | Gly | Phe | Tyr | Lys | Asn | |
| | | 145 | | | | | 150 | | | | | 155 | | | | |
| gtg | gtg | aag | att | caa | aag | cat | gtt | acc | ttc | aac | caa | gtg | aaa | ggc | att | 3949 |
| Val | Val | Lys | Ile | Gln | Lys | His | Val | Thr | Phe | Asn | Gln | Val | Lys | Gly | Ile | |
| | 160 | | | | | 165 | | | | | 170 | | | | | |
| ttc | ggc | ttc | act | gac | agc | gac | tgc | att | ggg | aag | atc | agt | ttt | cct | gcc | 3997 |
| Phe | Gly | Phe | Thr | Asp | Ser | Asp | Cys | Ile | Gly | Lys | Ile | Ser | Phe | Pro | Ala | |
| 175 | | | | 180 | | | | | 185 | | | | | 190 | | |
| atc | cag | gct | gct | ccc | tcc | ttc | agc | aac | tca | ttc | cca | cag | atc | ttc | cga | 4045 |
| Ile | Gln | Ala | Ala | Pro | Ser | Phe | Ser | Asn | Ser | Phe | Pro | Gln | Ile | Phe | Arg | |
| | | | 195 | | | | | 200 | | | | | 205 | | | |
| gac | agg | acg | gat | atc | cag | tgc | ctt | atc | cca | tgt | gcc | att | gac | cag | gat | 4093 |
| Asp | Arg | Thr | Asp | Ile | Gln | Cys | Leu | Ile | Pro | Cys | Ala | Ile | Asp | Gln | Asp | |
| | | | 210 | | | | | 215 | | | | | 220 | | | |
| cct | tac | ttt | aga | atg | aca | agg | gac | gtc | gcc | ccc | agg | atc | ggc | tat | cct | 4141 |
| Pro | Tyr | Phe | Arg | Met | Thr | Arg | Asp | Val | Ala | Pro | Arg | Ile | Gly | Tyr | Pro | |
| | | 225 | | | | | 230 | | | | | 235 | | | | |
| aaa | cca | gcc | ctg | ttg | cac | tcc | acc | ttc | ttc | cca | gcc | ctg | cag | ggc | gcc | 4189 |
| Lys | Pro | Ala | Leu | Leu | His | Ser | Thr | Phe | Phe | Pro | Ala | Leu | Gln | Gly | Ala | |
| | 240 | | | | | 245 | | | | | 250 | | | | | |
| cag | acc | aaa | atg | agt | gcc | agc | gac | cca | aac | tcc | tcc | atc | ttc | ctc | acc | 4237 |
| Gln | Thr | Lys | Met | Ser | Ala | Ser | Asp | Pro | Asn | Ser | Ser | Ile | Phe | Leu | Thr | |

```
                                                                                -continued
     255                 260                 265                 270
gac  acg  gcc  aag  cag  atc  aaa  acc  aag  gtc  aat  aag  cat  gcg  ttt  tct     4285
Asp  Thr  Ala  Lys  Gln  Ile  Lys  Thr  Lys  Val  Asn  Lys  His  Ala  Phe  Ser
                         275                 280                 285 gga  ggg  aga  gac  acc  atc  gag  gag  cac  agg  cag  ttt  ggg  ggc  aac  tgt     4333
Gly  Gly  Arg  Asp  Thr  Ile  Glu  Glu  His  Arg  Gln  Phe  Gly  Gly  Asn  Cys
                    290                 295                 300 gat  gtg  gac  gtg  tct  ttc  atg  tac  ctg  acc  ttc  ttc  ctc  gag  gac  gac     4381
Asp  Val  Asp  Val  Ser  Phe  Met  Tyr  Leu  Thr  Phe  Phe  Leu  Glu  Asp  Asp
               305                 310                 315 gac  aag  ctc  gag  cag  atc  agg  aag  gat  tac  acc  agc  gga  gcc  atg  ctc     4429
Asp  Lys  Leu  Glu  Gln  Ile  Arg  Lys  Asp  Tyr  Thr  Ser  Gly  Ala  Met  Leu
          320                 325                 330 acc  ggt  gag  ctc  aag  aag  gca  ctc  ata  gag  gtt  ctg  cag  ccc  ttg  atc     4477
Thr  Gly  Glu  Leu  Lys  Lys  Ala  Leu  Ile  Glu  Val  Leu  Gln  Pro  Leu  Ile
     335                 340                 345                 350 gca  gag  cac  cag  gcc  cgg  cgc  aag  gag  gtc  acg  gat  gag  ata  gtg  aaa     4525
Ala  Glu  His  Gln  Ala  Arg  Arg  Lys  Glu  Val  Thr  Asp  Glu  Ile  Val  Lys
                         355                 360                 365 gag  ttc  atg  act  ccc  cgg  aag  ctg  tcc  ttc  gac  ttt  cag  aag  ctt  gcg     4573
Glu  Phe  Met  Thr  Pro  Arg  Lys  Leu  Ser  Phe  Asp  Phe  Gln  Lys  Leu  Ala
                    370                 375                 380 gcc  gca  ctc  gag  cac  cac  cac  cac  cac  cac  tgagatccgg ctgctaacaa            4623
Ala  Ala  Leu  Glu  His  His  His  His  His  His
               385                 390 agcccgaaag gaagctgagt tggctgctgc caccgctgag caataactag cataacccct                   4683
tggggcctct aaacgggtct tgagggttt tttgctgaaa ggaggaacta tatccggat                     4742

<210> SEQ ID NO 7
<211> LENGTH: 392
<212> TYPE: PRT
<213> ORGANISM: Artificial Sequence
<220> FEATURE:
<223> OTHER INFORMATION: Cleavage Product T2 of recombinant human TrpRS

<400> SEQUENCE: 7

Met Ser Ala Lys Gly Ile Asp Tyr Asp Lys Leu Ile Val Arg Phe Gly
 1               5                  10                  15

Ser Ser Lys Ile Asp Lys Glu Leu Ile Asn Arg Ile Glu Arg Ala Thr
             20                  25                  30

Gly Gln Arg Pro His His Phe Leu Arg Arg Gly Ile Phe Phe Ser His
         35                  40                  45

Arg Asp Met Asn Gln Val Leu Asp Ala Tyr Glu Asn Lys Lys Pro Phe
     50                  55                  60

Tyr Leu Tyr Thr Gly Arg Gly Pro Ser Ser Glu Ala Met His Val Gly
 65                  70                  75                  80

His Leu Ile Pro Phe Ile Phe Thr Lys Trp Leu Gln Asp Val Phe Asn
                 85                  90                  95

Val Pro Leu Val Ile Gln Met Thr Asp Asp Glu Lys Tyr Leu Trp Lys
             100                 105                 110

Asp Leu Thr Leu Asp Gln Ala Tyr Gly Asp Ala Val Glu Asn Ala Lys
         115                 120                 125

Asp Ile Ile Ala Cys Gly Phe Asp Ile Asn Lys Thr Phe Ile Phe Ser
     130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
```

-continued

```
                165                 170                 175
Phe Thr Asp Ser Asp Cys Ile Gly Lys Ile Ser Phe Pro Ala Ile Gln
            180                 185                 190
Ala Ala Pro Ser Phe Ser Asn Ser Phe Pro Gln Ile Phe Arg Asp Arg
        195                 200                 205
Thr Asp Ile Gln Cys Leu Ile Pro Cys Ala Ile Asp Gln Asp Pro Tyr
    210                 215                 220
Phe Arg Met Thr Arg Asp Val Ala Pro Arg Ile Gly Tyr Pro Lys Pro
225                 230                 235                 240
Ala Leu Leu His Ser Thr Phe Phe Pro Ala Leu Gln Gly Ala Gln Thr
                245                 250                 255
Lys Met Ser Ala Ser Asp Pro Asn Ser Ser Ile Phe Leu Thr Asp Thr
            260                 265                 270
Ala Lys Gln Ile Lys Thr Lys Val Asn Lys His Ala Phe Ser Gly Gly
        275                 280                 285
Arg Asp Thr Ile Glu Glu His Arg Gln Phe Gly Gly Asn Cys Asp Val
    290                 295                 300
Asp Val Ser Phe Met Tyr Leu Thr Phe Phe Leu Glu Asp Asp Lys
305                 310                 315                 320
Leu Glu Gln Ile Arg Lys Asp Tyr Thr Ser Gly Ala Met Leu Thr Gly
                325                 330                 335
Glu Leu Lys Lys Ala Leu Ile Glu Val Leu Gln Pro Leu Ile Ala Glu
            340                 345                 350
His Gln Ala Arg Arg Lys Glu Val Thr Asp Glu Ile Val Lys Glu Phe
        355                 360                 365
Met Thr Pro Arg Lys Leu Ser Phe Asp Phe Gln Lys Leu Ala Ala Ala
    370                 375                 380
Leu Glu His His His His His His
385                 390

<210> SEQ ID NO 8
<211> LENGTH: 5
<212> TYPE: PRT
<213> ORGANISM: Homo sapiens

<400> SEQUENCE: 8

Ser Asn His Gly Pro
1               5

<210> SEQ ID NO 9
<211> LENGTH: 5
<212> TYPE: PRT
<213> ORGANISM: Homo sapiens

<400> SEQUENCE: 9

Ser Ala Lys Gly Ile
1               5

<210> SEQ ID NO 10
<211> LENGTH: 4
<212> TYPE: PRT
<213> ORGANISM: Homo sapiens

<400> SEQUENCE: 10

His Val Gly His
1

<210> SEQ ID NO 11
```

```
<211> LENGTH: 5
<212> TYPE: PRT
<213> ORGANISM: Homo sapiens

<400> SEQUENCE: 11

Lys Met Ser Ala Ser
 1               5

<210> SEQ ID NO 12
<211> LENGTH: 378
<212> TYPE: PRT
<213> ORGANISM: Homo sapiens

<400> SEQUENCE: 12

Ser Ala Lys Gly Ile Asp Tyr Asp Lys Leu Ile Val Arg Phe Gly Ser
 1               5                  10                  15

Ser Lys Ile Asp Lys Glu Leu Ile Asn Arg Ile Glu Arg Ala Thr Gly
            20                  25                  30

Gln Arg Pro His His Phe Leu Arg Gly Ile Phe Phe Ser His Arg
        35                  40                  45

Asp Met Asn Gln Val Leu Asp Ala Tyr Glu Asn Lys Lys Pro Phe Tyr
 50                  55                  60

Leu Tyr Thr Gly Arg Gly Pro Ser Ser Glu Ala Met His Val Gly His
 65                  70                  75                  80

Leu Ile Pro Phe Ile Phe Thr Lys Trp Leu Gln Asp Val Phe Asn Val
                85                  90                  95

Pro Leu Val Ile Gln Met Thr Asp Glu Lys Tyr Leu Trp Lys Asp
            100                 105                 110

Leu Thr Leu Asp Gln Ala Tyr Gly Asp Ala Val Glu Asn Ala Lys Asp
        115                 120                 125

Ile Ile Ala Cys Gly Phe Asp Ile Asn Lys Thr Phe Ile Phe Ser Asp
130                 135                 140

Leu Asp Tyr Met Gly Met Ser Ser Gly Phe Tyr Lys Asn Val Val Lys
145                 150                 155                 160

Ile Gln Lys His Val Thr Phe Asn Gln Val Lys Gly Ile Phe Gly Phe
                165                 170                 175

Thr Asp Ser Asp Cys Ile Gly Lys Ile Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
        275                 280                 285

Asp Thr Ile Glu Glu His Arg Gln Phe Gly Gly Asn Cys Asp Val Asp
290                 295                 300

Val Ser Phe Met Tyr Leu Thr Phe Phe Leu Glu Asp Asp Lys Leu
305                 310                 315                 320

Glu Gln Ile Arg Lys Asp Tyr Ser Gly Ala Met Leu Thr Gly Glu
                325                 330                 335
```

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
            355                 360                 365

Thr Pro Arg Lys Leu Ser Phe Asp Phe Gln
370                 375

<210> SEQ ID NO 13
<211> LENGTH: 401
<212> TYPE: PRT
<213> ORGANISM: Homo sapiens

<400> SEQUENCE: 13

Ser Asn His Gly Pro Asp Ala Thr Glu Ala Glu Asp Phe Val Asp
  1                 5                  10                  15

Pro Trp Thr Val Gln Thr Ser Ser Ala Lys Gly Ile Asp Tyr Asp Lys
            20                  25                  30

Leu Ile Val Arg Phe Gly Ser Ser Lys Ile Asp Lys Glu Leu Ile Asn
            35                  40                  45

Arg Ile Glu Arg Ala Thr Gly Gln Arg Pro His His Phe Leu Arg Arg
50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
                85                  90                  95

Glu Ala Met His Val Gly His Leu Ile Pro Phe Ile Phe Thr Lys Trp
            100                 105                 110

Leu Gln Asp Val Phe Asn Val Pro Leu Val Ile Gln Met Thr Asp Asp
            115                 120                 125

Glu Lys Tyr Leu Trp Lys Asp Leu Thr Leu Asp Gln Ala Tyr Gly Asp
            130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
                165                 170                 175

Phe Tyr Lys Asn Val Val Lys Ile Gln Lys His Val Thr Phe Asn Gln
            180                 185                 190

Val Lys Gly Ile Phe Gly Phe Thr Asp Ser Asp Cys Ile Gly Lys Ile
            195                 200                 205

Ser Phe Pro Ala Ile Gln Ala Ala Pro Ser Phe Ser Asn Ser Phe Pro
            210                 215                 220

Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                245                 250                 255

Ile Gly Tyr Pro Lys Pro Ala Leu Leu His Ser Thr Phe Phe Pro Ala
            260                 265                 270

Leu Gln Gly Ala Gln Thr Lys Met Ser Ala Ser Asp Pro Asn Ser Ser
            275                 280                 285

Ile Phe Leu Thr Asp Thr Ala Lys Gln Ile Lys Thr Lys Val Asn Lys
            290                 295                 300

His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe

```
                     325                 330                 335
Leu Glu Asp Asp Asp Lys Leu Glu Gln Ile Arg Lys Asp Tyr Thr Ser
            340                 345                 350

Gly Ala Met Leu Thr Gly Glu Leu Lys Lys Ala Leu Ile Glu Val Leu
        355                 360                 365

Gln Pro Leu Ile Ala Glu His Gln Ala Arg Arg Lys Glu Val Thr Asp
    370                 375                 380

Glu Ile Val Lys Glu Phe Met Thr Pro Arg Lys Leu Ser Phe Asp Phe
385                 390                 395                 400

Gln
```